United States Patent
LeBrun et al.

(10) Patent No.: US 7,070,981 B2
(45) Date of Patent: Jul. 4, 2006

(54) **GENE 763 OF PHYTOPATHOGENIC FUNGUS *MAGNAPORTHE GRISEA* AND USE THEREOF FOR IDENTIFYING FUNGICIDAL COMPOUNDS**

(75) Inventors: Marc-Henri LeBrun, Lyons (FR); Marie-Pascale Latorse, Sourcieux les Mines (FR)

(73) Assignee: Bayer CropScience S.A., Lyon (FR)

( * ) Notice: Subject to any disclaimer, the term of this patent is extended or adjusted under 35 U.S.C. 154(b) by 369 days.

(21) Appl. No.: 10/240,363

(22) PCT Filed: Mar. 26, 2001

(86) PCT No.: PCT/FR01/00907

§ 371 (c)(1),
(2), (4) Date: Apr. 14, 2003

(87) PCT Pub. No.: WO01/75115

PCT Pub. Date: Oct. 11, 2001

(65) Prior Publication Data

US 2004/0038359 A1    Feb. 26, 2004

(30) Foreign Application Priority Data

Mar. 31, 2000 (FR) ................... 00 04101

(51) Int. Cl.
*C12N 1/21* (2006.01)
*C12N 1/19* (2006.01)
*C12N 15/63* (2006.01)
*C12N 5/10* (2006.01)

(52) U.S. Cl. .............. 435/252.3; 435/254.11; 435/320.1; 435/325; 536/23.5

(58) Field of Classification Search ............ None
See application file for complete search history.

(56) References Cited

FOREIGN PATENT DOCUMENTS

WO    WO 99/13094    3/1999

OTHER PUBLICATIONS

"A BAC end sequencing framework to sequence the *Magnaporthe grisea* genome," XP002155631, Apr. 9, 1999.
"A BAC end sequencing framework to sequence the *Magnaporthe grisea* genome," XP002155632, Mar. 15, 1999.
"Molecular characterization of meaB, a novel gene affecting nitrogen metabolite repression in *Aspergillus nidulans*," Polley, et al., FEBS Letters 388 (1996), pp. 200-205.
"Molecular Approaches to Antifungal Molecule Discovery," Grosjean-Cournoyer, et al., Pesticide Chemistry and Bioscience: The Food-Environment Challenge, pp. 247-254 (1999).
"Regulatory Genes Controlling *MPG1* Expression and Pathogenicity in the Rice Blast Fungus *Magnaporthe grisea*," Lau and Hamer; The Plant Cell, vol. 8, pp. 771-781 (May 1996).

*Primary Examiner*—Robert A. Wax
(74) *Attorney, Agent, or Firm*—Connolly Bove Lodge and Hutz LLP

(57) ABSTRACT

The invention concerns a novel nucleic acid fragment of the genome of rice pathogenic fungus *Magnaporthe grisea* comprising a gene coding for a protein (hereafter referred to as gene 763) whereof the presence and integrity are indispensable for pathogenesis of said fungus with respect to rice and barley. The invention also concerns the promoter of said gene, the gene coding for protein 763, protein 763 and uses thereof for identifying potential biological targets for novel fungicide molecules and for isolating genes coding for proteins controlling biochemical functions essential to the pathogenesis of the fungus *Magnaporthe grisea* with respect to rice and barley. The invention further concerns compounds inhibiting pathogenesis of fungi related to the expression of gene 763.

16 Claims, 7 Drawing Sheets

```
M.grisea_    -----MTRSPSAEPS---KP--AKRKGTRSVSTLTPSQLARKRANDREAQ
N.crassa_    -----MARSPPAPTTGDNKPGTVKRKGTRSVSTLTPSQLARKRANDREAQ
             -----*-***--------**---************************

M.grisea_    RAIRARTKEHIERLEREVEELKSKQNRDETLQELIRKNKYLEKEIARLRE
N.crassa_    RAIRARTKELIERLQRELEESRGRENRDGMVRELLQKNKALEHEVRALRE
             ********_****_**_*------***---**_-***-**-*---***

M.grisea_    TYGIPTPPTSHPYAPSI---YDDSAVSSRTSSSPGQHSPDYHQVGEYGAS
N.crassa_    ALGIGNRPFPQSGYEVDGLQTSPSAVPGR-GASIPQGSTDYGAPTSFGSS
             --**---*------------******-----*--*-*-**-------**

M.grisea_    YMTTPEPSEPWTSVLP------CSNVSSPASS-GSAEEYGYI--PTSVP-
N.crassa_    YLPTPEPCEAWPPVVPVSSVTVSSVVSSPSSSTGHPDEYAASHVPTSVPS
             *---****-*-*--*-*--------*-****-**-----**----****-

M.grisea_    ----AGIEGLPPTSRVGACMK--YEDMDNENGYPRSNGVPMPP-TYMHQQ
N.crassa_    SLMDSSVMGQATGISCLDGMKVNYDEIEADRGYCPTS-VPQPQSSYLPQQ
             --------*---------**--****------**-----**-*------**

M.grisea_    QWPVPYSATVYYPQSPAL
N.crassa_    SWSM-YPTSTYYPQSPTV
             -**--*----*****--
```

Fig. 7

GENE 763 OF PHYTOPATHOGENIC FUNGUS *MAGNAPORTHE GRISEA* AND USE THEREOF FOR IDENTIFYING FUNGICIDAL COMPOUNDS

The present invention relates to a novel gene 763 which is essential to fungal pathogenesis. The invention relates to polynucleotides 763, to polypeptides 763, to host organisms expressing a polypeptide 763 and to uses thereof for identifying novel antifungal molecules.

The principle of using genes of pathogenic fungi, entirely or in part, in tests for identifying novel molecules active against these fungi is in itself) mown (in Antifungal Agents: Discovery and Mode of Action, G. K. Dixon, L. G. Coppong and D. W. Hollomon eds, BIOS Scientific Publisher Ltd, Oxford UK). With this aim, knowledge of the genome of a given pathogenic fungus constitutes an important step for the implementation of such tests. However, the simple knowledge of a given gene is not sufficient to attain this objective, it also being necessary for the gene chosen as a target for potential fungicidal molecules to be essential to the life of the fungus, inhibition thereof by the fungicidal molecule leading to death of the fungus, or essential to the pathogenesis of the fungus, inhibition thereof not being lethal for the fungus but simply inhibiting its pathogenic capacity. This second category of potential target genes for fungicidal molecules is particularly important for the development of a new generation of fungicidal products more favorable to the environment, which specifically attack only the pathogenic capacity of pathogenic fungi.

The present invention relates to the identification and cloning of a novel gene 763 which is essential for fungal pathogenesis. A mutant 763 of *Magnaporthe grisea*, in which the gene is inactivated, exhibits a pathogenesis reduced by 95%. Gen 763 encodes a transcription factor comprising a motif of the bZIP type, composed of a dominant basic sequence-specific DNA binding motif followed by another termed "leucine zipper motif", required for dimerization of the protein. This motif is characteristic of a vast family of proteins which regulate gene expression. The expression of gene 763 is detected during the early stages of plant infection. The invention also relates to the use of gene 763 for identifying novel antifungal molecules and the use of gene 763 for identifying other genes involved in fungal pathogenesis, the expression of which is regulated by 763.

DESCRIPTION OF THE SEQUENCE LISTING

SEQ ID No. 1: Gene 763 of *Magnaporthe grisea*
SEQ ID No. 2: cDNA of gene 763 of *Magnaporthe grisea*
SEQ ID No. 3: Polypeptide 763 of *Magnaporthe grisea*
SEQ ID No. 4: cDNA of gene 763 of *Neurospora crassa*
SEQ ID No. 5: Polypeptide 763 of *Neurospora crassa*

DESCRIPTION OF THE INVENTION

Polynucleotides

The present invention relates to the polynucleotides comprising a fungal gene 763. Gene 763 can be isolated from phytopathogenic fungi such as, for example, *Botrytis cinerea, Mycosphaerella graminicola, Stagnospora nodorum, Blumeria graminis, Colleotrichum lindemuthianum, Puccinia graminis, Leptosphaeria maculans, Fusarium oxysporum, Fusarium graminearum* and *Venturia inaequalis*. Advantageously, gene 763 is isolated from phytopathogenic fungi of the genus *Magnaporthe*. Preferably, the polynucleotides of the invention comprise a gene 763 of *Magnaporthe grisea*. Preferentially, the polynucleotides of the present invention comprise the coding sequence of a gene 763 of *Magnaporthe grisea.*

The term "polynucleotides 763" denotes all of the polynucleotides of the present invention, preferably the polynucleotides of the genomic sequence of 763, the polynucleotides of the cDNA sequence of 763, and also the polynucleotides encoding the polypeptides 763 of the present invention. The term "polynucleotides 763" also denotes recombinant polynucleotides comprising said polynucleotides.

According to the present invention, the term "polynucleotide" is intended to mean a single-stranded nucleotide chain, or the chain complementary thereto, or a double-stranded nucleotide chain, which may be of the DNA or RNA type. Preferably, the polynucleotides of the invention are of the DNA type, in particular double-stranded DNA. The term "polynucleotide" also denotes modified polynucleotides and oligonucleotides.

The polynucleotides of the present invention are isolated or purified from their natural environment. Preferably, the polynucleotides of the present invention can be prepared using the conventional molecular biology techniques as described by Sambrook et al. (Molecular Cloning: A Laboratory Manual, 1989) or by chemical synthesis.

The invention relates to polynucleotides comprising the genomic sequence of gene 763 of *Magnaporthe grisea* SEQ ID No. 1. This genomic sequence comprises 4 exons (positions 723–770, 925–1194, 1273–1554 and 1663–1778 of SEQ ID No. 1), 3 introns (positions 771–924, 1195–1272 and 1555–1662 of SEQ ID No. 1), and 5' and 3' regulatory sequences.

In a preferred embodiment of the invention, the polynucleotides of the genomic sequence of 763 comprise a polynucleotide chosen from the following polynucleotides:

a) the polynucleotide of SEQ ID No. 1,
b) a polynucleotide comprising at least one exon of SEQ ID No. 1;
c) a polynucleotide comprising a combination of exons of SEQ ID No. 1.

The present invention also relates to a polynucleotide comprising a 5' or 3' regulatory sequence of gene 763 of *Magnaporthe grisea*. In a first embodiment, the invention relates to a polynucleotide comprising the promoter of gene 763 of *Magnaporthe grisea*, the sequence of which is included between position 1 and position 705 of SEQ ID No. 1. In another embodiment, the invention relates to a polynucleotide comprising a biologically active fragment of the promoter gene 763 of *Magnaporthe grisea*, the sequence of which is included between position 1 and position 705 of SEQ ID No. 1.

The expression "biologically active fragment" is above intended to mean a polynucleotide having promoter activity, and more particularly promoter activity in fungi. The techniques which make it possible to evaluate the promoter activity of a polynucleotide are well known to those skilled in the art. These techniques conventionally involve the use of an expression vector comprising, in the direction of transcription, the polynucleotide to be tested and a reporter gene (see Sambrook et al., Molecular Cloning: A Laboratory dual, 1989).

The invention also relates to polynucleotides comprising the cDNA of 763 of *Magnaporthe grisea* of SEQ ID No. 2. The cDNA gene 763 of *Magnaporthe grisea* comprises the coding sequence of gene 763 and also a 5' UTR regulatory sequence and a 3' UTR regulatory sequence. The invention more particularly relates to polynucleotides comprising the coding sequence of gene 763 of *Magnaporthe grisea*, the sequence of which is included between position 17 and position 733 of SEQ ID No. 2.

The invention also extends to the polynucleotides comprising a polynucleotide chosen from the following polynucleotides:
a) the polynucleotide of SEQ ID No. 1;
b) the polynucleotide of SEQ ID No. 2;
c) the polynucleotide of SEQ ID No. 4;
d) a polynucleotide homologous to a polynucleotide as defined in a) or b) or c);
e) a polynucleotide capable of selectively hybridizing to a polynucleotide as defined in a) or b) or c).

According to the invention, the term "homologous" is intended to mean a polynucleotide having one or more sequence modifications compared to the reference sequence. These modifications may be deletions, additions or substitutions of one or more nucleotides of the reference sequence. Advantageously, the percentage homology will be at least 70%, 75%, 80%, 85%, 90%, 95% and preferably at least 98%, and more preferentially at least 99%, relative to the reference sequence. The methods for measuring and identifying homologies between nucleic acid sequences are well known to those skilled in the art. The PILEUP or BLAST programs (in particular Altschul et al., J. Mol. Evol. 36:290–300, 1993; Altschul et al., J. Mol. Biol. 215:403–10, 1990; Altshul et al., NAR 25:3389–3402, 1997) may, for example, be used. Preferably, the default parameters will be used. The invention therefore relates to polynucleotides comprising polynucleotides exhibiting at least 70%, 75%, 80%, 85%, 90%, 95%, 98% and preferably at least 98%, and more preferentially at least 99%, homology with the polynucleotides 763, the polynucleotides of SEQ ID Nos. 1–2 or the polynucleotides of SEQ ID No. 4. Preferably, the invention relates to a polynucleotide comprising a polynucleotide of at least 50, 100, 200, 300, 400, 500, 1 000 nucleotides exhibiting at least 70%, 75%, 80%, 85%, 90%, 95%, 98% and preferably at least 98%, and more preferentially at least 99%, homology with the polynucleotides 763, the polynucleotides of SEQ ID Nos. 1–2 or the polynucleotides of SEQ ID No. 4. Preferably, the polynucleotides homologous to a reference polynucleotide conserve the function of the reference sequence.

According to the invention, the expression "sequence capable of selectively hybridizing" is intended to mean the sequences which hybridize with the reference sequence at a level significantly greater than the background noise. The level of the signal generated by the interaction between the sequence capable of selectively hybridizing and the reference sequences is generally 10 times, preferably 100 times more intense than that of the interaction of the other DNA sequences generating the background noise. Stringent hybridization conditions which allow selective hybridization are well known to those skilled in the art. In general, the hybridization and washing temperature is at least 5° C. below the Tm of the reference sequence at a given pH and for a given ionic strength. Typically, the hybridization temperature is at least 30% for a polynucleotide of 15 to 50 nucleotides and at least 60° C. for a polynucleotide of more than 50 nucleotides. By way of example, the hybridization is carried out in the following buffer: 6×SSC, 50 mM Tris-HCl (pH 7.5), 1 mM EDTA, 0.02% PVP, 0.02% ficoll, 0.02% BSA, and 500 µg/ml denatured salmon sperm DNA. The washes are, for example, performed successively at low stringency in a 2×SSC, 0.1% SDS buffer, at medium stringency in a 0.5×SSC, 01% SDS buffer and at high stringency in a 0.1×SSC, 0.1% SDS buffer. The hybridization may, of course, be carried out according to other usual methods well known to those skilled in the art (see in particular Sambrook et al., Molecular Cloning: A Laboratory Manual, 1989). The invention therefore relates to polynucleotides comprising a polynucleotide capable of selectively hybridizing with the polynucleotide of SEQ ID Nos. 1–2 or the polynucleotide of SEQ ID No. 4. Preferably, the invention relates to a polynucleotide comprising a polynucleotide of at least 50, 100, 200, 300, 400, 500, 1 000 nucleotides, capable of selectively hybridizing with the polynucleotide of SEQ ID Nos. 1–2 or the polynucleotide of SEQ ID No. 4. Preferably, the polynucleotides which selectively hybridize to a reference polynucleotide conserve the function of the reference sequence.

Preferably, the polynucleotides of the present invention conserve the function of gene 763 of *Magnaporthe grisea* and encode a transcription factor which is essential to the pathogenesis of the fungus, and which is expressed at the beginning of the infectious state.

Preferentially, the polynucleotides of the present invention complement a mutant 763 of *Magnaporthe grisea* and restore its pathogenicity for rice and barley. A mutant 763 according to the invention is a mutant of *Magnaporthe grisea* in which the gene 763 of SEQ ID No. 1 is inactivated using techniques well known to those skilled in the art.

The present invention also relates to allelic variants or homologues of gene 763 of *Magnaporthe grisea*.

The present invention also relates to the identification and cloning of genes homologous to gene 763 of *Magnaporthe grisea* in other phytopathogenic fungi. Preferably, these homologous genes can be isolated or cloned from a phytopathogenic fungus chosen from *Botrytis cinerea, Mycosphaerella graminicola, Stagnospora nodorum, Blumeria graminis, Colleotrichum lindemuthianum, Puccinia graminis, Leptosphaeria maculans, Fusarium oxysporum, Fusarium graminearum* and *Venturia inaequalis*. A subject of the invention is thus the use of a polynucleotide or of a fragment of a polynucleotide of SEQ ID No. 1 and of SEQ ID No. 2 according to the invention, for identifying homologous genes in other phytopathogenic fungi. The techniques for cloning homologous genes 763 in other phytopathogenic fungi are well known to those skilled in the art. The cloning is carried out, for example, by screening cDNA libraries or genomic DNA libraries with a polynucleotide or a fragment of a polynucleotide of SEQ ID No. 1 and of SEQ ID No. 2. These libraries can also be screened by PCR using specific or degenerate oligonucleotides derived from SEQ ID No. 1 or from SEQ ID No. 2. The techniques for constructing and screening these libraries are well known to those skilled in the art (see in particular Sambrook et al., Molecular Cloning: A Laboratory Manual, 1989). Phytopathogenic fungus genes 763 may also be identified in the databases by nucleotide or protein BLAST using SEQ ID Nos. 1–3.

Preferably, the cloned genes conserve the function of gene 763 of *Magnaporthe grisea* and encode a transcription factor which is essential to the pathogenesis of the fungus, and which is expressed at the beginning of the infectious stage. The sequences of the cloned genes can be analyzed according to known methods in order to establish that they encode a fungal transcription factor and in particular in order to establish that they encode a polypeptide comprising a motif of the bZIP type, composed of a dominant basic sequence-specific DNA binding motif followed by another termed "leucine zipper motif", required for dimerization of the protein. Moreover, the techniques for establishing that a known gene is essential to the pathogenesis of a fungus are known to those skilled in the art. For example, the gene studied is inactivated in the fungus using conventional molecular biology techniques; mention will in particular be made of replacement of the gene with a mark r gene by homologous recombination. The decrease in pathogenesis of the fungus comprising the inactivated gene is analyzed using phenotypic tests. Preferably, the inactivation of the homologous gene causes a decrease in pathogenesis of at least 95%. The techniques for analyzing the expression of a gene in the various developmental stages of the fungus, and more particularly at the beginning of an infection, are also well known to those skilled in the art. Typically, total RNAs or (poly A+) are prepared from the various developmental stages of the fungus. These RNAs are then analyzed by RT-PCR or by Northern Blotting in order to determine the level of expression of the gone. Other techniques well known to those skilled in the art may be used in order to establish that the polynucleotides of the invention conserve the function of gene 763 of *Magnaporthe grisea*. Mention will be made in particular of complementation of mutants 763 followed by tests for restoration of the pathogenesis of the fungus.

A blast search in databases made it possible to identify a homologue of gene 763 of *Magnaporthe grisea* in *Neurospora crassa*. This novel gene was identified by blasting non-annotated genomic sequences. The cDNA of this *Neurospora* gene 763 corresponds to SEQ ID No. 4 and the *Neurospora* polypeptide 763 corresponds to SEQ ID No. 5.

A subject of the invention is also polynucleotides comprising a polynucleotide encoding a polypeptide chosen from the following polypeptides:

a) the polypeptide of SEQ ID No. 3;
b) the polypeptide of SEQ ID No. 5;
c) a polypeptide homologous to a polypeptide as defined in a) or b);
d) a biologically active fragment of a polypeptide as defined in a) or b).

Polypeptides

The present invention also relates to polypeptides 763 of a phytopathogenic fungus, and more particularly of *Magnaporthe grisea*. The term "polypeptides 763" denotes all the polypeptides of the present invention and also the polypeptides encoded by the polynucleotides of the present invention. The term "polypeptides 763" also denotes fusion proteins, recombinant proteins or chimeric proteins comprising these polypeptides. In the present description, the term "polypeptide" also denotes proteins and peptides, and also modified polypeptides.

The polypeptides of the invention are isolated or purified from their natural environment. The polypeptides may be prepared by various methods. These methods are in particular purification from natural sources, such as cells naturally expressing these polypeptides, production of recombinant polypeptides by suitable host cells and subsequent purification thereof, production by chemical synthesis or, finally, a combination of these various approaches. These various methods of production are well known to those skilled in the art. Thus, the polypeptides 763 of the present invention may be isolated from the fungi expressing polypeptides 763. Preferably, the polypeptides 763 of the present invention are isolated from recombinant host organisms expressing a heterologous polypeptide 763. These organisms are preferably chosen from bacteria, yeasts, fungi, animal cells or insect cells.

A subject of the present invention is a polypeptide comprising a polypeptide 763 of *Magnaporthe grisea* of SEQ ID No. 3. The invention also relates to polypeptides comprising a biologically active fragment or a homologue of the polypeptide 763 of SEQ ID No. 3.

In another embodiment, a subject of the present invention is a polypeptide comprising a polypeptide 763 of *Neurospora crassa* of SEQ ID No. 5. The invention also relates to polypeptides comprising a biologically active fragment or a homologue of the polypeptide 763 of SEQ ID No. 5.

The term "fragment" of a polypeptide denotes a polypeptide comprising part but not all of the polypeptide from which it is derived. The invention relates to a polypeptide comprising a fragment of at least 10, 15, 20, 25, 30, 35, 40, 50, 100, 200 amino acids of a polypeptide of SEQ ID No. 3.

The term "biologically active fragment" denotes a fragment of a polypeptide which conserves the function of the polypeptide from which it is derived. The biologically active fragments of the polypeptide of SEQ ID No. 3 thus conserve the function of the polypeptide 763 of *Magnaporthe grisea*. These biologically active fragments therefore have activity of a transcription factor which is functional in fungi. Preferentially, this activity is essential to the pathogenesis of the fungus.

The term "homologue" denotes a polypeptide which may have a deletion, an addition or a substitution of at least one amino acid. A subject of the invention is a polypeptide having at least 75%, 80%, 85%, 90%, 95%, 98% and preferentially at least 99% of amino acids identical with a polypeptide of SEQ ID No. 3 or of SEQ ID No. 5. The methods for measuring and identifying homologies between polypeptid s or proteins are known to those skill d in the art. The UWGCG package and the BESTFITT program may, for example, be used to calculate the homologies (Devereux et al., Nucleic Acid Res. 12, 387–395, 1984). The default parameters are preferably used.

Preferably, these homologous polypeptides conserve the same biological activity as the polypeptide 763 of *Magnaporthe grisea* of SEQ ID No. 3. Preferentially, these polypeptides therefore have a fungal transcription factor activity. Preferentially, this activity is essential to the pathogenesis of the fungus. In a preferred embodiment, these homologous polypeptides may be isolated from phytopathogenic fungi. Preferably, these polypeptides are expressed in phytopathogenic fungi at the beginning of plant infection.

A subject of the invention is also a fusion polypeptide comprising a polypeptide 763 as described above fused to a reporter polypeptide. The reporter polypeptide allows rapid detection of the expression of a polypeptide 763 in a fungus or in another host organism. Among the polypeptides which may thus be fused with a polypeptide 763, mention will be made in particular of GFP (green fluorescent protein) and the GUS (β-glucuronidase) protein. These fusion proteins and their constructs are well known to those skilled in the art.

Expression Cassettes, Vectors and Host Organisms

Gene 763 can be expressed in various host organisms, such as bacteria, yeasts, fungi, animal cells or insect cells. Gene 763 can be expressed in a host organism under the control of the promoter 763 of the present invention or under the control of a heterologous promoter.

Expression Cassettes

According to an embodiment of the invention, a polynucleotide encoding a polypeptide 763 is inserted into an expression cassette using cloning techniques well known to those skilled in the art. This expression cassett comprises the elements required for the transcription and translation of the sequences encoding the polypeptide 763. Advantageously, this expression cassette comprises both elements for making a host cell produce a polypeptide 763 and elements required for regulating this expression. In a first embodiment, the expression cassettes according to the invention comprise, in the direction of transcription, a promoter which is functional in a host organism, gene 763 or the sequence encoding gene 763, and a sequence which is a terminator sequence in said host organism. Preferentially, the expression cassette comprises, in the direction of transcription, a promoter which is functional in a host organism, a polynucleotide chosen from the following polynucleotides:

a) a polynucleotide encoding the polypeptide 763 of SEQ ID No. 3 or encoding a biologically active fragment of the polypeptide 763 of SEQ ID No. 3;
b) a polynucleotide, the sequence of which is included between position 17 and position 733 of SEQ ID No. 2;
c) a polynucleotide of SEQ ID No. 1;
d) a polynucleotide of SEQ ID No. 2;
e) a polynucleotide encoding the polypeptide 763 of SEQ ID No. 5 or encoding a biologically active fragment of the polypeptide 763 of SEQ ID No. 5;
f) a polynucleotide of SEQ ID No. 4;
g) a polynucleotide homologous to a polynucleotide as defined in b), c), d) or f);
h) a polynucleotide capable of specifically hybridizing to a polynucleotide as defined in b), c), d) or f);

and a sequence which is a terminator sequence in said host organism.

Any type of promoter sequence may be used in the expression cassettes according to the invention. The choice of promoter will in particular depend on the host organism chosen for expressing the gene of interest. Some promoters allow constitutive expression whereas other promoters are, on the contrary, inducible. Among the promoters which are functional in fungi, mention will be made in particular of that of *Aspergillus nidulans* glyceraldehyde-3-phosphate dehydrogenase (Roberts et al., Current Genet. 15:177–180, 1989). Among the promoters which are functional in bacteria, mention will be made in particular of the T7 bacteriophage RNA polymerase (Studier et al., Methods in enzymology 185:60–89, 1990). Among the promoters which are functional in yeasts, mention will be made in particular of that of the Gal1 gene (Elledge et al., Proc. Nat. Acad. Sciences, USA. 88:1731–1735, 1991) or the GAL4 and ADH promoters of *S. cerevisiae*. Among the promoters which are functional in insect cells, mention will be made in particular of the polyhedrin promoter of the baculovirus AcMNPV (Weyer et al., J. Gene. Virol. 72:2967–2974, 1991). Among the promoters which are functional in animal cells, mention will be made of the metallothionein promoter and viral and adenoviral promoters. All these promoters are described in the literature and are well known to those skilled in the art.

The promoter 763 may be used to express a heterologous gene in a host organism and in particular in fungi. A subject of the invention is therefore also expression cassettes comprising the promoter of a gene 763, functionally associated with a sequence encoding a heterologous protein, allowing expression of said protein in fungi. Preferably, the expression cassette according to the invention comprises, in the direction of transcription, a polynucleotide, the sequence of which is included between position 1 and position 705 of SEQ ID No. 1, or a biologically active fragment of the polynucleotide, the sequence of which is included between position 1 and position 705 of SEQ ID No. 1, the sequence encoding a heterologous polypeptide and terminator sequence which is functional in fungi. Any gene of interest may be expressed in a host organism under the control of a promoter 763. Preferably, the promoter 763 is used for expressing a heterologous gene in fungi. The activity of the promoter 763 under various conditions may be evaluated using a reporter gene such as the GUS (β-glucuronidase), GFP (green fluorescent protein), LUC (luciferase), CAT (chloramphenicol transferase) or β-galactosidase (lacZ) reporter gene.

In a preferred embodiment of the invention, the promoter 763 is functionally associated with the coding sequence of a marker gene. Expression of the marker gene allows the transformed organisms to be selected by virtue of their resistance to antibiotics or to herbicides for example. Mention will in particular be made of the coding sequences for a gene for tolerance to an antibiotic or a herbicide, such as the genes for resistance to hygromycin (hph: Punt et al., 1987), to bleomycin (ble: Drocourt, 1990) or to the herbicide bialaphos (Bar: Pall and Brunelli, 1993).

The expression cassettes according to the present invention may also include any other sequence required for expressing gene 763 or the heterologous gene, such as, for example, regulatory elements or signal sequences for addressing the polypeptide 763. Any regulatory sequence making it possible to increase the level of expression of the coding sequence inserted into said expression cassette may in particular be used. According to the invention, it is in particular possible to use, in combination with the promoter regulatory sequence, other regulatory sequences, which are located between the promoter and the coding sequence, such as transcription activators (enhancers). As a signal for membrane addressing in the host organisms, mention will in particular be made of that of protein A in bacteria (Nilsson et al., Methods in Enzymology 198:3, 1991).

A large variety of terminator sequences can be used in the expression cassettes according to the invention, these sequences allowing termination of transcription and polyadenylation of the mRNA. Any terminator sequence which is functional in the host organism selected may be used.

A subject of the present invention is also a polynucleotide comprising an expression cassette according to the invention; advantageously, the expression cassettes according to the present invention are inserted into a vector.

Vectors

The present invention therefore also relates to replication or expression vectors for transforming a host organism, comprising at least one polynucleotide 763 or an expression cassette according to the present invention. This vector may in particular consist of a plasmid, a cosmid, a bacteriophage or a virus, into which a polynucleotide 763 or an expression cassette according to the invention is inserted. The techniques for constructing these vectors and for inserting a polynucleotide of the invention into these vectors are well known to those skilled in the art. In general, any vector capable of maintaining itself, of self-replicating or of propagating in a host cell, and in particular in order to induce the expression of a polynucleotide or of a polypeptide, may be used. Advantageously, the vectors according to the invention comprise at least one origin of replication in order for them to replicate in a host organism. Preferably, the vectors of the invention also comprise at least one selectable marker, such as a gene for resistance to an antibiotic. Mention will in particular be made of vectors such as pBluescript (Stratagene, La Jolla, Calif.), pTrcHis (Invitrogen, La Jolla, Calif.) and baculovirus-derived expression vectors, such as those derived from the *Autographica californica* polyhedrovirus (AcMNPv). A preferred system combining a baculovirus and an insect cell is the pV111392 baculovirus/Sf21 cell system (Invitrogen, La Jolla, Calif.). Fox expression in animal cells, adenovirus-derived vectors are in particular used. Those skilled in the art will choose the suitable vectors in particular as a function of the host organism to be transformed and as a function of the transformation technique used. The methods for transforming host organisms are well known to those skilled in the art (Inoue et al., Gene 96:23–28, 1990; Fincham, Microbiological Reviews 53:148–170, 1989).

The vectors of the present invention are in particular used to transform a host organism for the purpose of replication of the vector and/or expression of a polypeptide 763 in said host organism. The invention relates to a method for preparing a polypeptide M763, comprising the following steps:

a host organism is transformed with an expression vector comprising an expression cassette according to the invention, the polypeptides M763 produced by the host organism are isolated, The recombinant polypeptides 763 produced by a host organism transformed with a polynucleotide can be purified or isolated according to methods known to those skilled in the art. The polypeptides M763 can be expressed in a host organism in the form of fusion proteins. Mention will in particular be made of the vectors pGEX for expressing fusion proteins comprising glutathione S-transferase (GST). Thes fusion proteins are easily purified by adsorption on glutathione-agarose beads. The GST group can then be removed by digestion with protease Xa. Other systems for expressing and purifying fusion proteins are known to those skilled in the art.

Host Organisms

A subject of the present invention is also a method for transforming a host organism by integrating into said host organism at least one polynucleotide 763 or an expression cassette or a vector according to the invention. The polynucleotide may be integrated into the genome of the host organism or may replicate stably in the host organism. The methods for transforming host organisms are well known to those skilled in the art and widely described in the Literature (Inoue et al., Gene 96:23–28, 1990; Fincham, Microbiological Reviews 53:148–170, 1989).

The present invention also relates to a host organism transformed with a polynucleotide 763, an expression cassette or a vector according to the invention. According to the invention, the term "host organism" is in particular intended to mean any lower or higher, unicellular or pluricellular organism, in particular chosen from bacteria, yeasts, fungi, animal cells and insect cells. Advantageously, the bacteria are chosen from *Escherichia coli* and *Bacillus subtilis*, the yeasts are chosen from *Pichia pastoris* and *Saccharomyces cerevisae*, the insect cells are chosen from *Spodoptera frugiperda* and *Drosophila melanogaster*, and the animal cells are chosen from CHO, HeLa and COS cells.

The techniques for constructing vectors, for transforming host organisms and for expressing heterologous proteins in these organisms are widely described in the literature (Ausubel F. M. et al., "Current Protocols in Molecular Biology" Volumes 1 and 2, Greene Publishing Associates and Wiley-Interscience, 1989; T. Maniatis, E. F. Fritsch, J. Sambrook, Molecular Cloning A Laboratory Handbook, 1982).

The present invention also relates to the use of polynucleotides 763 and of polypeptides 763 for identifying genes involved in fungal pathogenesis and for identifying novel fungicidal molecules which inhibit fungal pathogenesis.

Inhibition of Fungal Pathogenesis

Fungi in which gene 763 is inactivated or inhibited exhibit a pathogenesis which is reduced by 95%. The invention relates to methods for inhibiting fungal pathogenesis by inactivating or inhibiting the expression of gene 763. Preferably, the fungi are chosen from *Botrytis cinerea, Mycosphaerella graminicola, Stagnospora nodorum, Blumeria graminis, Colleotrichum lindemuthianum, Puccinia graminis, Leptosphaeria maculans, Fusarium oxysporum, Fusarium graminearum* and *Venturia inaequalis.*

Preferably, the invention relates to methods for inhibiting the pathogenesis of a fungus, said methods comprising inhibiting the expression of a polynucleotide 763 according to the invention in said fungus, or inhibiting the expression of a polypeptide 1763 according to the invention in said fungus or inhibiting the biological activity of a polypeptide 763 according to the invention in said fungus. Preferably, this inhibition affects specifically the expression of gene 763 and the biological activity of the polypeptide 763. The invention does not therefore relate to the methods comprising the general inhibition of gene expression in the fungus. It will be understood that the inhibition of the expression of gene 763 may, however, lead to the inhibition of other genes.

Various methods well known to those skilled in the art may be used to inhibit fungal pathogenesis by inhibiting the expression of gene 763 in these fungi. In one embodiment of the invention, gene 763 is inactivated by insertional mutagenesis or by homologous recombination (gene replacement or "knock out" techniques). In another embodiment of the invention, the expression of a polypeptide 763 is inhibited by expressing an antisense polynucleotide of gene 763 in the fungi. In a third embodiment of the invention, the expression of gene 763 is inhibited by an inhibiting compound.

The level of expression of a polynucleotide 763 or of a polypeptide 763 in the fungi can be measured according to techniques described in the literature. Mention will in particular be made of Northern blotting, PCR and DNA arrays (DNA chips) for the polynucleotides and Western blotting for the polypeptides. These techniques are well known to those skilled in the art.

Identification of Novel Fungicidal Molecules which Inhibit Fungal Pathogenesis

Inactivation of gene 763 in *Magnaporthe grisea*, a pathogenic fungus of rice, leads to a 95% decrease in the pathogenesis of this fungus. Moreover, it has been possible to identify homologous genes in other fungi. Consequently, compounds which inhibit the expression of gene 763 or the activity of the polypeptide 763 in fungi can be used to inhibit fungal pathogenesis.

The invention therefore relates to methods for identifying compounds which inhibit fungal pathogenesis, comprising a step of identifying a compound which specifically inhibits the expression of a polynucleotide 763 in said fungus, or a step of identifying a compound which inhibits the expression of a polypeptide 763 in said fungus or a step of identifying a compound which inhibits the biological activity of a polypeptide 763 in said fungus.

Preferably, the fungi are chosen from *Botrytis cinerea, Mycosphaer 11a graminicola, Stagnospora nodorum, Blumeria graminis, Colleotrichum lindemuthianum, Puc-*

*cinia graminis, Leptosphaeria maculans, Fusarium oxysporum, Fusarium graminearum* and *Venturia inaequalis*.

The polynucleotides 763, the polypeptides 763, the vectors and the host organisms of the present invention may thus be used in various screening assays in order to identify novel antifungal compounds.

Identification of Inhibitors which Bind to the Protein 763

Molecules which directly inhibit the activity of the polypeptide 763 might inhibit the pathogenesis of the fungus and lead to the development of novel fungicides.

The invention therefore relates to a method for identifying compounds which inhibit fungal pathogenesis, comprising the following steps:
  bringing said compound into contact with a polypeptide 763, and
  detecting the binding of said compound to said polypeptide; and preferentially, the method also comprises a step in which it is determined whether said compound inhibits fungal pathogenesis.

Any method for preparing a polypeptide 763 and for purifying it or for isolating it may be used in the methods of the present invention.

Preferably, the polypeptide 763 is expressed in a heterologous expression system (for example bacterium, yeast, animal cell or insect cell) by means of a polynucleotide 763 according to the invention; the simplified purification of the polypeptide 763 then makes it possible to identify novel molecules which bind to the protein 763. Said molecules are identified using methods well known to those skilled in the art, in particular methods of physical detection of the binding of the compounds tested to the protein 763 (BIACORE system; Karlson & al., J. of Biomolecular Interaction Analysis, Special Issue Drug Discovery: 18–22).

Identification of Inhibitors of Gene 763 Expression Regulators

Molecules which inhibit the expression of gene 763 may also inhibit the pathogenesis of the fungus and lead to the development of novel fungicides. In the present invention, the expression "inhibition of the expression of gene 763" denotes the inhibition of the expression of a polynucleotide 763 and also the inhibition of the expression of a polypeptide 763 in host organisms, and preferentially in phytopathogenic fungi.

A subject of the invention is also a method for identifying compounds which inhibit fungal pathogenesis, comprising the following steps;
  bringing said compound into contact with a host organism transformed with a polynucleotide or a vector according to the invention such that this host organism expresses a reporter gene under the control of the promoter of gene 763; and
  detecting the inhibition of the expression of said reporter gene.

Preferentially, the method also comprises a step in which it is determined whether said compound inhibits fungal pathogenesis.

The use of a polynucleotide according to the invention, comprising the promoter 763 associated with the coding sequence of a reporter gene (GUS or GFP for example) makes it possible to measure the promoter activity of the promoter 763 in a fungal cell or in a host cell. This method makes it possible to identify compounds which inhibit the activity of the promoter 763 and therefor the expression of gene 763 at the transcriptional level. A recombined strain comprising the above gene is thus used to identify molecules which inhibit the expression of gene 763, which manifests itself by inhibition of the expression of the reporter protein of the recombined strain under conditions for expression of gene 763. This type of assay is well known to those skilled in the art and described in the literature, in particular Axiotis et al. (1995, pp. 1–7 in Antifungal Agents: Discovery and Mode of Action. G. K. Dixon, L. G. Coppong and D. W. Hollomon, eds, BIOS Scientific Publisher Ltd. Oxford, UK).

In another embodiment, the invention relates to a method for identifying compounds which inhibit fungal pathogenesis, comprising the following steps:
  bringing said compound into contact with a host organism transformed with a polynucleotide according to the invention or a vector according to the invention, said host organism expressing a polypeptide 763; and
  detecting the inhibition of the expression of said polypeptide 763.

Preferably, the polypeptide 763 is a fusion polypeptide comprising a reporter polypeptide such as GUS of GFP, the expression of which is easily measured. Preferentially, the method also comprises a step in which it is determined whether said compound inhibits fungal pathogenesis. This method makes it possible to identify compounds which inhibit the expression of gene 763 at the transcriptional level or at the translational level. A recombined strain expressing a polypeptide 763, and preferably a polypeptide 763 fused to a reporter, is thus used to identify molecules which inhibit the expression of gene 763, which manifests itself by inhibition of the expression of the polypeptide 763 of the recombined strain under the conditions for expression of gene 763.

The present invention therefore relates to a method for identifying compounds which inhibit fungal pathogenesis associated with expression of gene 763, said method consisting in subjecting a compound, or a mixture of compounds, to an assay suitable for identifying compounds which inhibit said fungal pathogenesis, and in selecting the compounds which react positively to said assay and, where appropriate, in isolating them and then in identifying them.

Preferentially, the suitable assay is an assay as defined above.

Preferably, a compound identified according to these methods is then tested for its antifungal properties and for its ability to inhibit the pathogenesis of the fungus for plants, according to methods known to those skilled in the art. Preferentially, the compound is evaluated using phenotypic tests, such as pathogenesis assays on leaves or on whole plants.

According to the invention, the term compounds is intended to mean any chemical compound or mixture of chemical compounds, including peptides and proteins.

According to the invention, the expression "mixture of compounds" is understood to mean at least two different compounds, such as, for example, the (dia)stereoisomers of a molecule, mixtures of natural origin derived from the extraction of biological material (plants, plant tissues, bacterial cultures, yeast or fungal cultures, insects, animal tissues, etc.) or reaction mixtures which are unpurified or totally or partly purified, or else mixtures of products derived from combinatorial chemistry techniques.

Finally, the present invention relates to novel compounds which inhibit fungal pathogenesis associated with expression of gene 763, in particular the compounds identified by the method according to the invention and/or the compounds derived from the compounds identified by the method according to the invention.

Preferentially, the compounds which inhibit fungal pathogenesis associated with expression of gene 763 are not general enzyme inhibitors. Also preferentially, the compounds according to the invention are not compounds already known to have fungicidal activity and/or activity on fungal pathogenesis.

A subject of the invention is also a method for treating plants against a phytopathogenic fungus, characterized in that it comprises treating said plants with a compound identified by a method according to the invention.

The present invention also relates to a method for preparing a compound which is an inhibitor of fungal pathogenesis, said method comprising the steps of identifying a compound which inhibits fungal pathogenesis associated with the expression of gene 763, by the identification method according to the invention, and then preparing said identified compound by the usual methods of chemical synthesis, of enzymatic synthesis and/or of extraction of biological material. The step of preparing the compound may be preceded, where appropriate, by an "optimization" step by which a compound derived from the compound identified by the identification method according to the invention is identified, said derived compound then being prepared by the usual methods.

The examples below make it possible to illustrate the invention without, however, seeking to limit the scope thereof.

All the methods or operations described below in these examples are given by way of examples and correspond to a choice, made from the various methods available for achieving the same result. This choice has no bearing on the quality of the result and, consequently, any suitable method may be used by those skilled in the art in order to achieve the same result. Most of the DNA fragment engineering methods are described in "Current Protocols in Molecular Biology" Volumes 1 and 2, F. M. Ausubel et al., published by Greene Publishing Associates and Wiley-Interscience (1989), or in Molecular Cloning, T. Maniatis, E. F. Fritsch and J. Sambrook (1982). The methods specific for fungi are described in Sweigard et al. (Fungal Genetics Newsletter, 44:52–53, 1997) for the fungal transformation vectors used, in Orbach (Gene 150:159–162, 1994) for constructing a cosmid library, in Sweigard et al. (Fungal Genetics Newsletter, 37:4–5, 1990) for preparing fungal genomic DNAs, and in Agnan et al. (Fungal Genetics and Biology, 21:292–301, 1997).

DESCRIPTION OF THE FIGURES

FIG. 1: Autoradiogram of hybridization, with a probe pAN7.1, of the transfer onto nylon membranes of genomic DNA digestions of the mutant 763. (E:EcoR1; A:ApaI; C:ClaI; K:KpnI).

FIG. 7: Alignment of the protein 763 of *Magnaporthe grisea* and of the homologous protein of *Neurospora crassa*.

Figure 2:
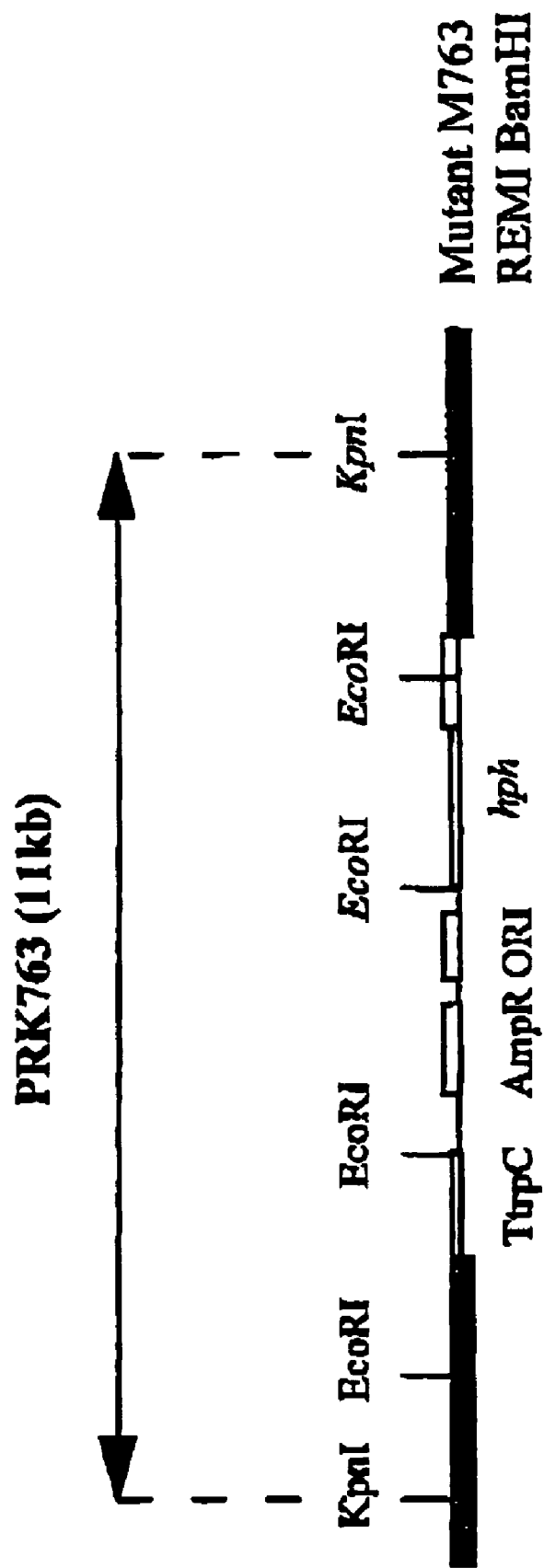
FIG. 2: "Plasmid rescue" in the mutant 763. Genomic DNA of the mutant 763 (in bold) with insertion site of the plasmid. The positions of the EcoRI and KpnI sites on the genomic DNA are arbitrary.

Alignment produced using the clustal-W program. (*: identical amino acids).

EXAMPLES

The strategy employed to achieve the identification and characterization of gene 763 essential to the pathogenesis of *M. grisea* comprised two main points:

1) Inactivation of a gene essential to pathogenesis by random insertion into its nucleotide sequence of a foreign DNA fragment (insertional mutagenesis).
2) Recovery and characterization of the fungal nucleotide sequence thus modified, and then demonstration of its involvement in the pathogen sis of the fungus with respect to rice and to barley.

The methodological steps to be successively surmounted are as follows:

1) Obtaining a collection of fungal isolates having randomly integrated a foreign DNA fragment into their genome (transformants). In this case, the foreign DNA is a plasmid comprising the hph gene of *Escherichia coli*, which allowed them to be selected on the basis of hygromycin resistance. It was introduced into the fungal genome by protoplast transformation.
2) Searching for transformants which are nonpathogenic with respect to rice and to barley, among the collection (pathogenesis mutants). The criterion selected for non-pathogenesis of a transformant was the inability to cause foliar lesions subsequent to inoculation of spores of this transformant into rice and barley plants.
3) Genetically demonstrating the inactivation of a pathogenesis gene by the plasmid in the mutants incapable of infecting rice and barley. This involved establishing complete genetic linkage between the hygromycin-resistance characteristic, which reflects the presence of the plasmid in the genome of the mutant, and that of nonpathogenesis, which reflects the inactivation of a gene essential to the infectious capacity of the fungus. This degree of linkage was evaluated by analysis of segregation of the hygromycin-resistance and nonpathogenesis characteristics in the descendents of a cross between the mutant studied and a wild-type strain pathogenic with respect to rice and to barley and having a mating type compatible with that of the mutant.
4) Recovering the genomic region of the fungus at which the insertion of the mutating plasmid occurred. The principle consisted in isolating a DNA fragment of the mutant comprising both plasmid and genomic sequences, detectable by virtue of a hybridization experiment with a probe of plasmid origin. The genomic component included in this fragment was then used to isolate the complete wild-type genomic region according to the same principle.

5) Demonstrating that the genomic region next to the point of insertion of the plasmid contains the pathogenesis gene. If the pathogenesis gene sought is in the genomic region next to the point of insertion of the plasmid, the introduction thereof into the genome of the mutant isolate, using a plasmid vector comprising another selectable marker, should make it possible to restore pathogenesis by complementation of the function made deficient by insertion of the first plasmid. Proof of this is provided if the spores of at least one transformant obtained through this experiment are capable of causing as many foliar lesions as the wild-type strain.

6) Characterizing the genomic sequence of the fungus in the proximity of the point of insertion of the plasmid. The product from sequencing the genomic region next to the point of insertion of the plasmid is analyzed with sequence processing programs, so as to attempt to demonstrate therein a nucleotide sequence capable of being translated into peptide sequence (open reading frame). This search is carried out on the basis of searching for consensus signals for initiation and termination of translation to protein. Proof of the existence of an open reading frame (and therefore of a gene) in this region was provided by cloning the corresponding transcriptional unit, by screening a library of DNAs complementary to messenger RNAs (cDNAs) with a probe produced from a fragment of this region. The sequence of this cDNA makes it possible to determine with precision the size and the primary sequence of the corresponding protein, and also the position of possible introns in the genomic sequence of the gene.

Example 1

Insertional Mutagenesis

Protoplast transformation with an integrative plasmid carrying a selectable marker was used as an insertional mutagenesis tool in order to search for the pathogenesis genes of the rice-parasite ascomycete fungus *Magnaporthe grisea*. The conditions for culturing, for obtaining protoplasts, for transformation and also for purifying and storing *Magnaporthe grisea* transformants are described by Silué et al. (Physiol. Mol. Plant Pathol., 53, 239–251, 1998). The transformation was carried out with 1 µg of plasmid pAN7.1 (Punt et al., Gene 78: 147–156), 1987) and $10^7$ protoplasts of the *M. grisea* strain P1.2. This strain originates from the collection of the phytopathology laboratory of the CIRAD [International Center for Cooperation in Agronomic Research for Development] in Montpellier. The transformants were selected by incorporating hygromycin into the agar culture media, at the concentrations of 240 ppm for the primary selection medium and of 120 ppm for the secondary selection medium.

Example 2

Screening the Collection of Transformants and Identifying the Nonpathogenic Mutant 763

A) Pathogenesis Assays on Leaves under Survival Conditions

The pathogenesis assays were carried out on two varieties of rice, Maratelli and Sariceltick, and one variety of barley, Express. Maratelli are varieties which are very sensitive to blast disease and which do not have genes for resistance to the strain P1.2. The barley varieties are extremely sensitive to blast disease. The rice was grown at 25° C. during the day and 15° C. at night with a hygrometry of greater than 70%, the barley was grown under cold conditions (20–22° C.). Rice and barley leaf fragments (2.5 cm) were removed from the median part of the youngest leaf of plants about twenty days old. These fragments were placed in multicompartment dishes containing water with 1% agar supplemented with 2 mg/l of kinetin, a medium which allows them to survive for 14 days. It is important to note that rice develops a strong physiological resistance to blast disease during periods of great heat. This resistance may be attenuated by giving the plants nitrogen-based fertilizer: two waterings with a solution of ammonium sulfate at 5 g/$m^2$, one week apart. The second watering takes place 2 to 3 days before inoculation.

The conditions for sporulation and for preparing *M. grisea* spore inoculum are described by Silué at al. (mentioned above). The inoculation was performed using a wet cotton-wool bud soaked in a suspension of spores and passed over the leaf fragments under survival conditions. The amount of spores deposited was estimated by depositing a drop of the suspension onto a glass slide. The symptoms were observed after 4–7 days of incubation at 24° C., 100% hygrometry. Each transformant was tested on four rice leaf fragments of each variety and four of barley during the first screening. The transformant 763 shows a decrease in pathogenesis quantified at 95% of the number of lesions caused by the wild-type strain. The transformant 763 was inoculated a second time, in order to confirm its phenotype, with a suspension of spores having a concentration adjusted to $10^5$ spores per ml. The results are given in the table below.

TABLE 1

Pen tration of the mutant 763 into barley leaves
Inoculation of barley leaves with drops of 35 microliters containing spores (500 000 spores/ml)

| | |
|---|---|
| Exp. 1 | 48 h after inoculation, many surfac appressoria, few penetrations, some infectious hyphae visible, |
| | 6 days, no visible lesion, brown coloration at the point of contact of the drop |
| Exp. 2 | 48 h after inoculation, many surface appressoria, penetration not observed |
| | 4 days, no visible lesion, brown coloration at the point of contact of the drop |
| Exp. 3 | 48 h after inoculation, many surface appressoria, few penetrations, infectious hyphae visible in the leaf, colonization greatly slowed compared to P12 |

B) Pathogenesis Assays on Whole Plants

In order to confirm the phenotype of the nonpathogenic mutant 763 detected by inoculation of leaves under survival conditions, the department of phytopathology of the CIRAD at Montpellier performed inoculations of whole plants with the spores of this mutant. The two rice cultivars sensitive to the P1.2 strain, Maratelli and Sariceltick were sown and cultured under glass. Three nitrogen applications were performed during the first three weeks of culturing (at 5, 10 and 20 days after sowing). The inoculation by spraying a suspension of spores takes place 10 to 15 days after giving nitrogen for the last time, depending on the degree of maturity of the plants. The spore concentration was determined by counting with a Thoma cell and adjusted to a value of 20 000 spores/ml. The suspensions of spores of the mutant 763 and of the nontransformed strain P1.2 were sprayed onto thirty plants, in a proportion of 1 ml of spore suspension per plant, with an aerograph. One leaf from each of these plants was collected for counting the number of lesions, after they had developed (5 to 7 days). A 93% decrease in pathogenesis was also observed on whole plants (see table below).

TABLE 2

Spraying a spore suspension onto whol plants (ric. vari ty Sariceltick)

|  | P12 (wild-type strain) | Mutant 763 | Decrease compared to P12 |
|---|---|---|---|
| Exp. 1 | | | |
| Spores 25 000 sp/ml | 42 lesions per leaf lesion size: 3.5 mm² | 7 lesions per leaf lesion size: 0.5 mm² | −85% −85% |
| Exp. 2 | | | |
| Spores 100 000 sp/ml | 30 lesions per leaf | 2 lesions per leaf | −93% |

Example 3

Phenotypic Analysis of the Mutant 763

The mutant 763 is affected by a decrease in pathogenesis quantified at 93% of the number of lesions caused by the wild-type strain, without its ability to sporulate being lessened. In addition, while the rare lesions observed were clearly visible and made up of a necrotic area surrounded by a brownish border (typical symptom of blast disease), they were all small in size and nonsporulating, contrary to those caused by the wild-type strain (−90% at the surface). An infection assay on injured leaves shows that the progression of the hyphae of this mutant, in planta, remains limited to the area of injury. Cytological analysis of the infection in this mutant shows that the mutant manages to penetrate through the epidermal cell wall in barley, but it is then rapidly blocked in its progression.

The physiology and morphology of the conidia and of the mycelium of the transformant 763 are apparently normal. Its ability to differentiate appressoria on barley epidermis, as on artificial hydrophobic surfaces (PVC, Teflon, PET), is not different from that of the wild-type strain.

The growth of this mutant was also studied in the presence of salts and drugs which interfere with assimilation of nitrogen compounds. This involved determining whether it exhibited the phenotype of loss of metabolic repression of nitrogen, a characteristic of the mutant meaB of *Aspergillus nidulans* (see later, molecular analysis; Polley and Caddick, 1996). In this fungus, the metabolic repression of nitrogen results, in the presence of ammonium or of L-glutamine, in inhibition of the genes required for acquiring and using other nitrogen sources. The mutation mead is characterized by its resistance to methylammonium (a toxic inducer of metabolic repression of nitrogen) but also by its resistance to parafluorophenylalanine and by its hypersensitivity to nitric toxicity. The mutant 763 does not have a phenotype different from that of the wild-type strain under all the conditions tested. 763 also grows normally on minimum medium (MM).

Example 4

Genetic and Molecular Analysis of the Mutant 763

20 ascospores at random and a tetrad derived from the cross M4x763 were analyzed. The results of this analysis appear in the table below and show that hygromycin resistance cosegregates with loss of pathogenic capacity: the mutated pathogenesis gene is tagged with the plasmid pAN7.1 in 763.

TABLE 3

Analysis of the descendents of the cross M4x763

| Ascospore | Hyg. | Path. |
|---|---|---|
| Parenteral tetrad | | |
| 1 | s | + |
| 2 | s | + |
| 3 | s | + |
| 4 | s | + |
| 5 | R | − |
| 6 | R | − |
| 7 | R | − |
| 8 | N.D | N.D. |
| Ascospores at random | | |
| 1 | s | + |
| 2 | N.D. | N.D. |
| 3 | R | − |
| 4 | R | − |
| 5 | R | − |
| 6 | R | − |
| 7 | R | − |
| 8 | S | + |
| 9 | R | − |
| 10 | R | − |
| 11 | R | − |
| 12 | s | + |
| 13 | s | + |
| 14 | s | + |
| 15 | s | + |
| 16 | R | − |
| 17 | R | − |
| 18 | R | − |
| 19 | s | + |
| 20 | s | + |

Figure 1:
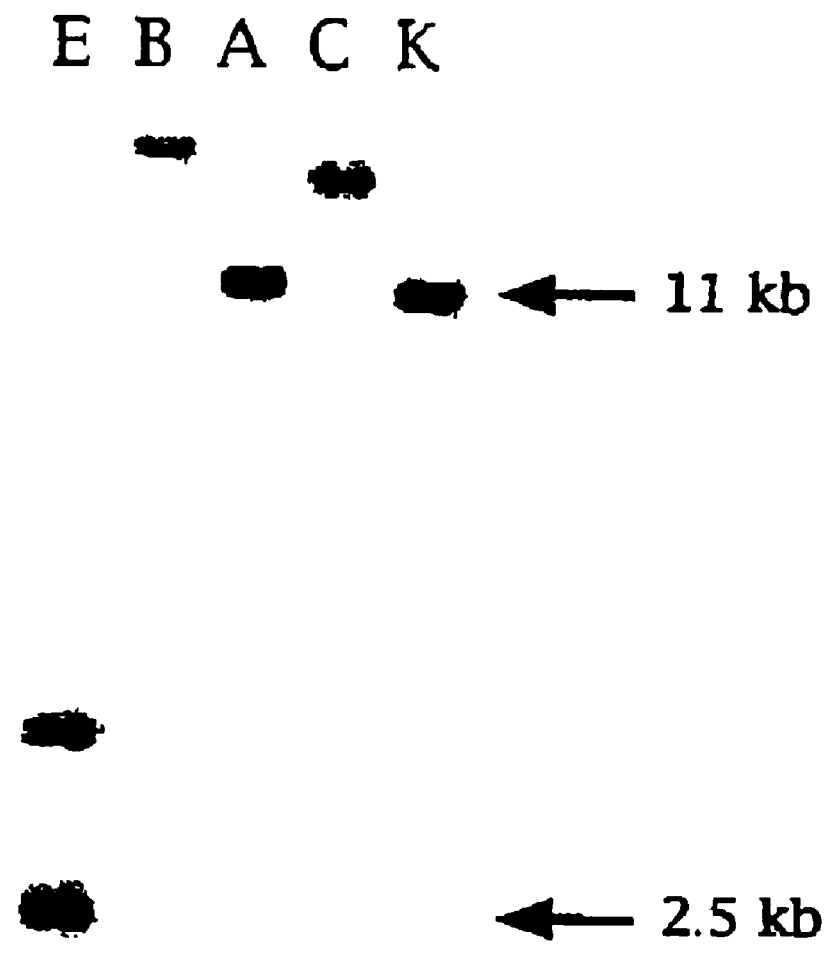

The number of copies of the plasmid pAN7.1 present in the genome of this transformant and the relative position of the point of integration were determined by hybridization with a plasmid probe (see FIG. 1). Three types of restriction enzyme were used depending on the number of cleavages desired: EcoRI (2 cleavages); BamHI (1 cleavage); ApaI, ClaI and KpnI (no cleavage). The hybridization profiles of the restriction fragments obtained show that this transformant comprises only one copy of the plasmid (3 EcoRI fragments, a single fragment for BamHI, ApaI, ClaI and KpnI). Moreover, the single BamHI hybridization fragment is greater than 6.75 kb in size. This indicates that the copy of the plasmid integrated into the genome of this transformant does not possess at its ends the two BamHI sites expected subsequent to transformation in the presence of this restriction enzyme. According to the analysis performed on many transformants derived from REMI transformations, it is probable that the integration of the plasmid led to short deletions in one or in the two sticky ends of the plasmid BamHI site, thus creating no BamHI restriction site at the junctions between the plasmid DNA and the genomic DNA of the transformant. With regard to the digestions with the enzymes which do not cleave in the sequence of pAN7.1 (ApaI, ClaI and KpnI), the smallest restriction fragment containing the entire plasmid was obtained in the lane corresponding to the KpnI digestion (11 kb in size). An additional experiment consisting of hybridization of SspI restriction fragments of the genomic DNA of the transformant 763 with a pUC19 probe was able to show that the sequences of the origin of replication of the plasmid in *E. coli* and of the ampicillin resistance gene were intact.

Example 5

Cloning and Characterization of the Pathogenesis Gene 763

The "plasmid rescue" technique (Timberlake, 1991) was used to clone the genomic regions located at the point of insertion of the plasmid. Due to its small size, the 11 kb KpnI fragment identified in the molecular analysis of the mutant was chosen to carry out this experiment (FIG. 2). A restriction analysis of the plasmid DNA of 4 ampicillin-resistant colonies obtained was performed. A colony bearing the expected plasmid (PRK763) was streaked and multiplied for the purpose of a DNA maxi preparation. An NdeI-SspI genomic DNA fragment of PRK763, 0.4 kb in size, located subsequent to sequencing the regions of genomic origin of this plasmid, was used to probe the cosmid library of the strain 96/0/76. The cosmids which hybridized with this fragment were isolated (21C7 and 35F3).

Figure 3:
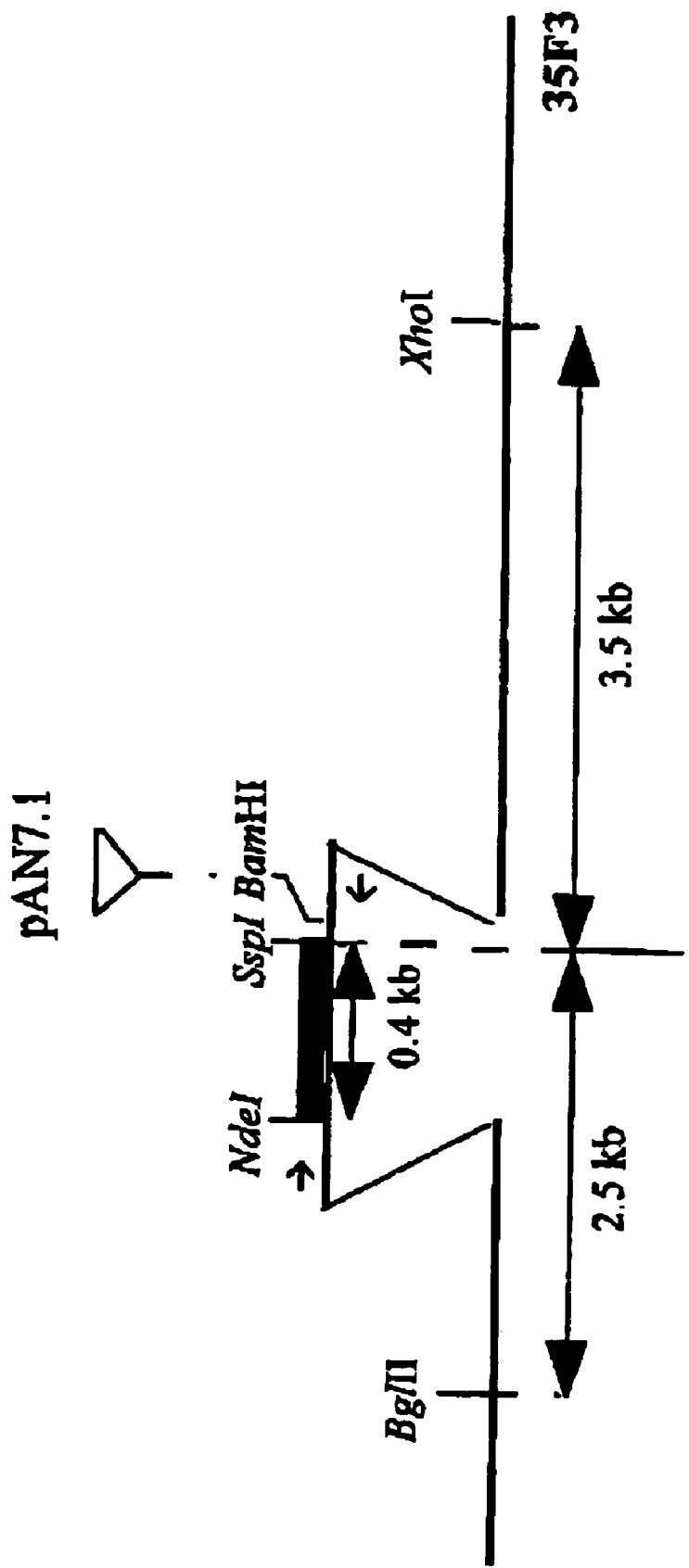
FIG. 3: Insertion locus of the plasmid pAN7.1 and BglII-XhoI restriction fragment (6 kb) complementing the mutant m763. The position of the genomic probe (0.4 kb) derived from PRK763 is indicated in bold. The arrows indicate the position of the PCR primers for amplifying the point of insertion of the plasmid into the wild-type strain. The point of insertion of the plasmid pAN7.1 is also indicated.

A 6 kb XhoI-BglII restriction fragment of the cosmid 35F3 which hybridizes with the NdeI-SspI restriction fragment of PRK763 was cloned into the plasmid pCB1265 (FIG. 3). This construct, called PC763 was introduced into the genome of the mutant 763 by protoplast transformation. A pathogenesis assay on detached leaves showed that the phosphinothricin-resistant transformants obtained have the same degree of virulence as the wild-type strain.

The library of complementary DNAs from the messenger RNAs of genes expressed in a culture in complete liquid medium was screened with the NdeI-SspI fragment of PRK763. Two types of clone approximately 2 kb long were recovered. One was shorter than the other by 113 bp at its 5' end, but 16 bp longer at its 3' end, this being just before the terminal polyadenylated sequence. This polyadenylated sequence was present at the 3' ends of the two types of clone isolated. Comparison of this cDNA sequence with that of the corresponding wild-type genomic DNA made it possible to demonstrate 3 introns of, respectively, 153, 78 and 108 pb. The positions of the translation initiation and termination signals in the cDNA sequence define an open reading frame 714 pb long. It begins 25 bp from the 5' end of the sequence of the longest cDNA clone and ends 1.22 kb from the 3' end of the sequence of this same clone. This long 3'-terminal untranslated sequence comprises many potential termination signals in the three possible reading frames.

The search for proteins with sequences homologous to that of P763 was carried out with the sequence alignment program BLASTP 2.0.8 (Altschul et al., 1997) in all the available databases using the default parameters. The only proteins which exhibit a significant degree of homology with the pathogenesis protein 763 of *Magnaporthe grisea* are the putative transcription factor MEAB of *Aspergillus nidulans* and also the transcription factors GCN4 and YAP1 of *Saccharomyces cerevisiae*.

Figure 4:
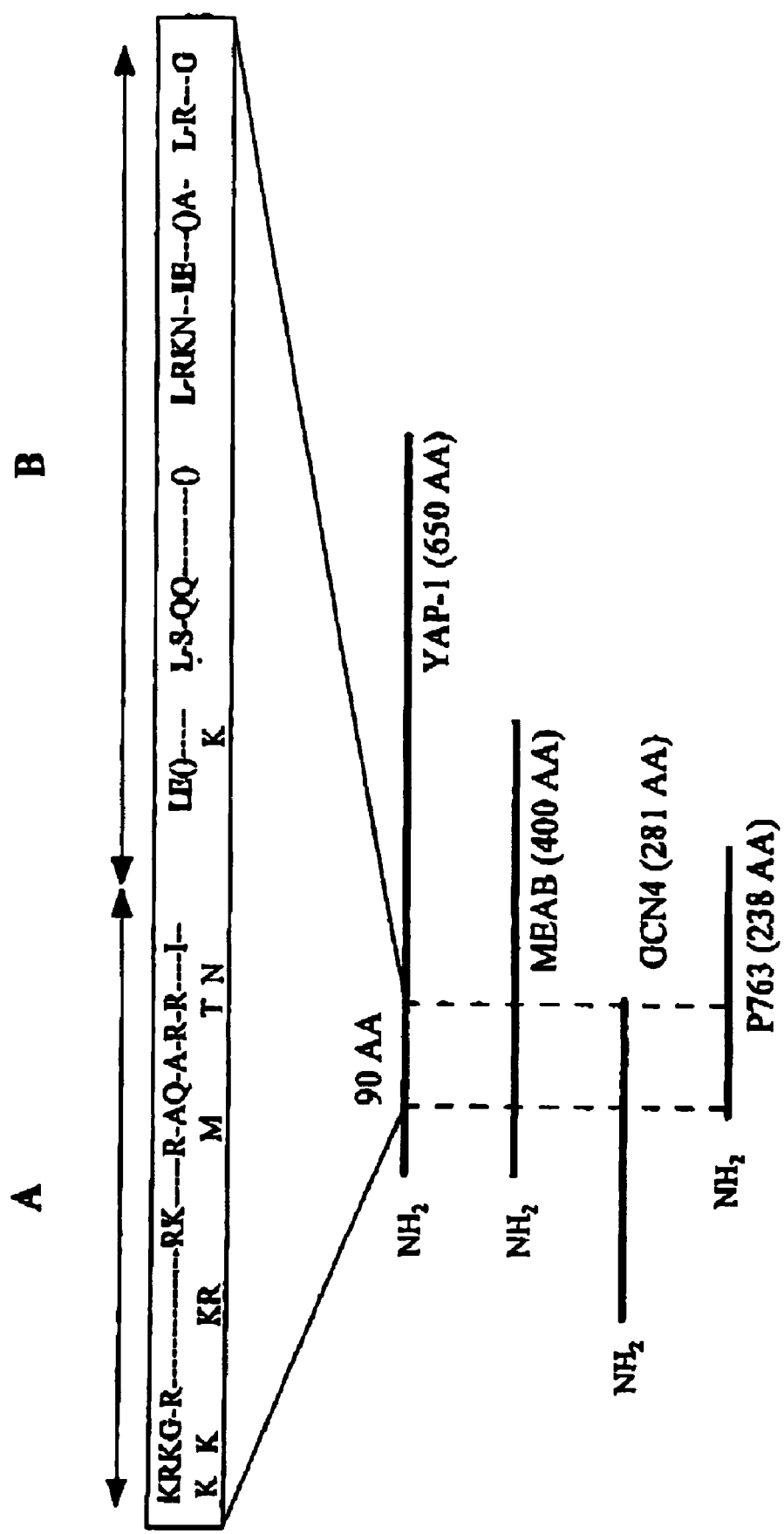
FIG. 4: Identification of a basic "leucin zipper" domain. Consensus obtained by alignment of the sequence of the protein P763 with those of the transcription factors YAP-1 and GCN4 of *Saccharomyces cerevisiae* and MEAB of *Aspergillus nidulans*. This domain comprises a basic domain (A) and a "leucine zipper" domain per se (B).

MEAB is thought to be involved in the control of nitrogen assimilation depending on the nature of the available sources of this element (Polley and Caddick, FEBS letters 388: 200–205, 1996). By virtue of its sequence, MEAB is related to the family of eukaryotic transcription factors of the bZIP type, composed of a dominant basic sequence-specific DNA binding motif following by another termed "leucine zipper motif", required for dimerization of the protein. The degree of similarity between P763 and MEAB is at a maximum in the amino-terminal portion of their sequences, that corresponding to the bZIP domain. Apart from this region, the MEAB sequence is longer (400 AA versus 238 in P763) and bears little resemblance to that of P763 in its carboxy-terminal portion (FIG. 4).

TABLE 4

Search for proteins homologous to the deduced protein of gene 763 (Blast P version 2.0.8)

| Score E | % identity and homology at the level of the b-ZIP domain (63 amino acids) | |
|---|---|---|
| 0.00009 | 38% and 54% | MeaB putative transcription factor of *A. nidulans* with b-ZIP |
| 0.002 | 31% and 55% | YAP1, transcription factor of *S. cerevisae* with b-ZIP |
| 0.002 | 40% and 55% | GCN4, transcription factor of *S. cerevisae* with b-ZIP |

Figure 5:
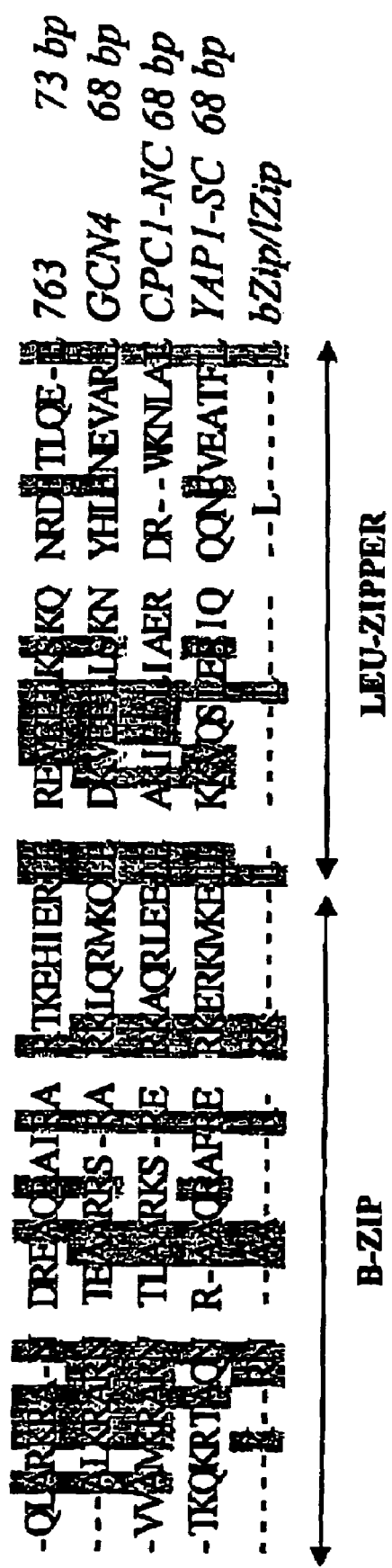
FIG. 5: Consensus obtained by alignment of the sequence of the protein 763 of *Magnaporthe grisea* with those of the transcription factors YAP-1 and GCN4 of *Saccharomyces cerevisiae* and CPC-1 of *Neurospora crassa*.
Figure 6:
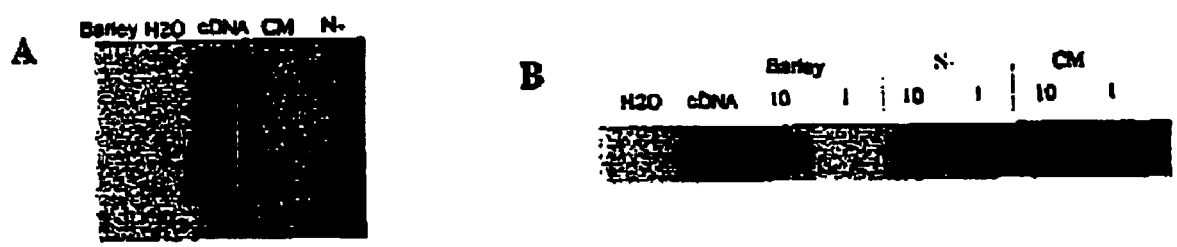
FIG. 6: Autoradiogram of hybridization, with a probe consisting of the cDNA of gene 763, of Southern membranes of the products of RT-PCR and nested-PCR amplification of the mRNA of this gene under various conditions.

The phenotypic analysis of the mutant 763 as a function of its behavior with respect to several drugs which interfere with nitrogen metabolism leads to the notion that the gene tagged with the plasmid in the mutant 763 is not the equivalent of MEAB in *Magnaporthe grisea*. The sequence of the bZIP domain of P763 aligns partially in the same search with those of two transcription factors of *Saccharomyces cerevisiae*, GCN4 (protein regulating expression of amino acid biosynthesis genes; Hinnebusch, PNAS 81:6442–6446, 1984) and YAP1 (activator of transcription of genes for cellular defense against oxidative stress; Schnell et al., Curr. Genet. 21(4–5):269–73 1992), and with the CPC-1 gene of *Neurospora crassa* (FIG. 5). Genes with a sequence homologous to that of the GCN4 gene were identified in the filamental fungi *Neurospora crassa* (Paluh et al., PNAS 85 (11) 3728–3732, 1988) with the CPC-1 gene and *Cryphonectria parasitica* (Wang et al., Fungal Genet. Biol. 23(1):81–94, 1998), and are different from gene 763 although related.

Example 6

Expression of the Pathogenesis Gene 763

A Northern blot prepared with 10 μg of RNAs extracted from samples of mycelium grown under several conditions (liquid culture in complete medium or in minimum medium) was hybridized, unsuccessfully, with a probe corresponding to the sequence of the cDNA of gene 763.

An RT-PCR experiment was carried out with primers located on both sides of the putative translation termination signal (defined by virtue of the analysis of the cDNA sequence) and 5 μg of total RNA extracted from mycelium from a liquid culture in complete medium. The amplification product, detected by hybridation with a probe 763, was cloned and sequenced. It shows no differences in size or in sequence with the cDNA clones isolated previously, in particular in the portion corresponding to the untranslated 3' sequence of the messenger RNA of the gene.

A nested RT-PCR experiment was carried out with 5 μg of RNA from infected barley leaves extracted 20 hours after inoculation and a secondary amplification was performed with a second pair of internal primers. An amplification product was detected by hybridization with a probe 763, revealing expression of this gene during the early steps of host colonization (FIG. 6).

The invention claimed is:

1. A polynucleotide, characterized in that it comprises a polynucleotide chosen from the following polynucleotides:
   a) the polynucleotide of SEQ ID No. 1;
   b) the polynucleotide of SEQ ID No. 2; and
   c) the polynucleotide, the sequence of which is included between position 17 and position 733 of SEQ ID No. 2.

2. The polynucleotide as claimed in claim 1, characterized in that it encodes a transcription factor which is functional in fungi.

3. The polynucleotide as claimed in claim 1, characterized in that it encodes a transcription factor which is essential to fungal pathogenesis for plants.

4. A polynucleotide, characterized in that it comprises a polynucleotide encoding the polypeptide of SEQ ID No. 3.

5. A polynucleotide, characterized in that it comprises the promoter of gene 763, the sequence of which is included between position 1 and position 705 of SEQ ID No. 1.

6. An expression cassette, characterized in that it comprises, in the direction of transcription:
   a) a promoter which is functional in a host organism;
   b) a polynucleotide as claimed in claim 1; and
   c) a sequence which is a terminator sequence in said host organism.

7. An expression cassette, characterized in that it comprises, in the direction of transcription:
   a) a promoter which is functional in a host organism;
   b) a polynucleotide encoding the polypeptide 763 or SEQ ID No. 3; and
   c) a sequence which is a terminator sequence in said host organism.

8. An expression cassette, characterized in that it comprises, in the direction of transcription:
   a) a polynucleotide as claimed in claim 5; and
   b) a reporter gene; and
   c) a terminator sequence.

9. A vector comprising a polynucleotide as claimed in claim 1.

10. An isolated hot cell transformed with a polynucleotide as claimed in claim 1.

11. A method for transforming isolated host cells by integrating into said isolated host cells at least one polynucleotide as claimed in claim 1.

12. A vector comprising an expression cassette as claimed in claim 6.

13. An isolated host cell transformed with an expression cassette as claimed in claim 6.

14. An isolated host cell transformed with a vector as claimed in claim 9.

15. A method for transforming isolated host cells by integrating into said isolated host cells an expression cassette as claimed in claim 6.

16. A method for transforming isolated host cells by integrating into said isolated host cells a vector as claimed in claim 9.

* * * * *

UNITED STATES PATENT AND TRADEMARK OFFICE
CERTIFICATE OF CORRECTION

| | |
|---|---|
| PATENT NO. | : 7,070,981 B2 |
| APPLICATION NO. | : 10/240363 |
| DATED | : July 4, 2006 |
| INVENTOR(S) | : Marc-Henri LeBrun et al. |

It is certified that error appears in the above-identified patent and that said Letters Patent is hereby corrected as shown below:

In the Claims:

In Claim 7, at column 31, line 57, "b) a polynucleotide encoding the polypeptide 763 or SEQ" should be -- b) a polynucleotide encoding the polypeptide 763 of SEQ --.

In Claim 10, at column 32, line 40, "An isolated hot cell transformed with a polynucleotide" should read -- An isolated host cell transformed with a polynucleotide --

In Claim 11, at column 32, line 43, "integrating into said isolated host cells at least one poly-" should read -- integrating into said isolated host cell at least one poly- --

In Claim 15, at column 32, line 52, "integrating into said isolated host cells an expression cas-" should read -- integrating into said isolated host cell an expression cas- --

UNITED STATES PATENT AND TRADEMARK OFFICE
CERTIFICATE OF CORRECTION

PATENT NO.         : 7,070,981 B2
APPLICATION NO. : 10/240363
DATED              : July 4, 2006
INVENTOR(S)        : March-Henri LeBrun et al.

It is certified that error appears in the above-identified patent and that said Letters Patent is hereby corrected as shown below:

In Claim 16, at column 32, line 55, "integrating into said isolated host cells a vector as claimed" should read -- integrating into said isolated host cell a vector as claimed --

Signed and Sealed this

Twentieth Day of February, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 2995
<212> TYPE: DNA
<213> ORGANISM: Magnaporthe grisea
<220> FEATURE:
<221> NAME/KEY: promoter
<222> LOCATION: (1)..(705)

<400> SEQUENCE: 1

```
actacccac cacagagacg cgcttgcagt atttgacgct aaccagaaag ctaggtaccc      60
aattgccagg ggtcagtaag ccaggggttgg cgcaacaagt aggtacgtac ttcccttccc   120
tgtttgaatt aaaaaaagat taaaaaaaaa aaggtacata gtacataatt acctactttc   180
catgcttgta ctgtggtaca tgctcgcatc gatctccgat ccactgagtc tggcccccac   240
caccctgga ctcttgctgc tgcaagtcct cgacaacctc gtcacgggct tcagtagccc   300
tgctgctccc ttgatccttg cctgccgggg gagagcgaga gagcccttgg atcatataat   360
aagctcgaca gaccctccag tgggaccatc agttgcacac atcaagcttg gggccctact   420
gtatgcctga aatcgaatca aaagacgaga ggtagactac catccaagcg cagatacacc   480
ttgatcgact ccatagcctc cttctccgat ccatccacca ctcatatcaa tccgtgtgcc   540
caagcctccc gcttctctcg ctctctccct cttttctctc ttgcatcttc tccttactta   600
taattcacat cttcactcat cataaccatc tccaaccatg gcaatgtata tgccctcaac   660
cgcatcttcg acgacacaca ttaggtctcc ctctggaacc cccatagact ctccacaccg   720
agatgactcg atcaccatcc gccgagccaa gcaagcctgc caagcggaag ggtaagtcat   780
gacttgggga gctatcttcc ccacgcagag cccacacaac agagtcatta cgcacccagc   840
tactcggtac ttgggggcat tatgcggctc ttggtcagca gtatctcaac tgacgccatt   900
gccaattatg ttgtttcaaa ataggtactc gtagcgtctc gactttgacg ccgtcccaac   960
tggctaggaa gagggcaaac gacagagaag cacagagggc cattcgtgcg cggacaaagg  1020
aacacatcga acgactcgaa agggaggtcg aagagctcaa gagcaagcag aaccgcgacg  1080
agaccctcca agaactcatc aggaagaaca agtaccttga aaggagatt gccaggctgc   1140
gcgagactta tggcatcccc accccgccaa catctcaccc atatgcgccg tccagtgagt  1200
gcactctcgc tcatacactg ctttgtaatt ttgccataga attacatggc taaccgggct  1260
tttctaacac agtctacgac gactctgcag tttccagccg gacatcatca tcttttgggc  1320
aacattcgcc agactaccat caggtcggag agtatggagc ttcctacatg acaaccccg   1380
agccttccga accgtggaca tcagtcttac cttgctccaa tgtttcaagc ccagcatcgt  1440
ccggaagtgc agaagaatac ggatacatcc cgaccagtgt tcccgccgga attgaaggac  1500
tccctcccac gtcgcgtgtt ggtgcctgca tgaaatatga ggatatggat aacggtgagc  1560
agtacctcgg tcgcaaataa tattgcaggc atggccacaa acctgtgt taaacagcga    1620
taatcgaacc acgagaccaa gctgacagcg aatgctatgt agaaacgga taccccgaa     1680
gcaacgcgt cccgatgccc ccaacctata tgcaccagca gcagtggccc gtaccataca   1740
gtgcaaccgt ttactacccc caatcgccgg ctctctgagc ggctaagggt catttggctc  1800
ccctccgtcg ctggtgagga gccaagtcgg gaccggagat gttaaatagt gttagccgcc  1860
accgtgtcac gacaatggtc tcacaaaatc aatccggcga cgcccgaaat gggcaaaaac  1920
```

-continued

```
ttgaattcaa agagacgaaa gcgaacgacg aattggacga cagagaacat cgaacccgac    1980
ctccttcgac tcgacccagt catcatttcg gttgatcaag aaattattct agaaaaccca    2040
aacgccggtt ttcgagacag cattagccaa ttttcttgct cattaacccg agactttgaa    2100
tgcattagcg tgagggagtg ggccagcggc ggtaacaaac aaaccaggca taactccaac    2160
gggatttgtc tgttcggatg ttccagcgcg gggacaacat catcaaggcc ttgaacattc    2220
gaccgatatt cgatcagatc agttcctcac cgccgaactc ccgaagctcg gcacgataaa    2280
ccctgaagcc attgtcacct gaaaacattc gcctttttt tttgttattc cgatgctcgt     2340
tcgcaacact acgttttagt tcgacctgtc acacattgcc gccgcgcacg tgtgccacca    2400
ctagtacagc ttgttaccgg accgaacaac gttttttcg ccaccgtgcg accctggtcc     2460
caagtggctt ggtgttgttg cttgcaaaaa aaacctccga caaccaagt cccccgggct     2520 ttattagtgt atgtcatcac gcaccccaca agagcctccc gtcactttgc tgtcagcatt    2580
ttgatggcag gcggggtgac cggcgtgaac ggccaaaagg cgtaggcttt gcgcagtctc    2640
tccaacaact ttaaagggca attgcgctta gccttggcca gaggtgtctt agctgggata    2700
aaaaaaacac atattctatt cttatttcgt ttccttgcgc tagcgtactg caacaatttt    2760
catataattt ttacaccaca atttagggag gttggctgat ttggacggcg gcgtcgtgga    2820
ggttactcat atatcggcgt atcaagaaag ctcattacca aagctgtatt tgcttttttgt   2880 ttcttgtata tatagactgc attgctcttg tcttgttcat atggagtgga cttgtctttg    2940
tgtggttgga gtctgggagc atattattgg gtgtgaataa cataggttgg gaatc         2995
```

```
<210> SEQ ID NO 2
<211> LENGTH: 1969
<212> TYPE: DNA
<213> ORGANISM: Magnaporthe grisea
<220> FEATURE:
<221> NAME/KEY: 5'UTR
<222> LOCATION: (1)..(16)
<220> FEATURE:
<221> NAME/KEY: CDS
<222> LOCATION: (17)..(730)
<220> FEATURE:
<221> NAME/KEY: 3'UTR
<222> LOCATION: (731)..(1969)

<400> SEQUENCE: 2
```

```
agactctcca cacgag atg act cga tca cca tcc gcc gag cca agc aag cct    52
               Met Thr Arg Ser Pro Ser Ala Glu Pro Ser Lys Pro
                 1               5                  10 gcc aag cgg aag ggt act cgt agc gtc tcg act ttg acg ccg tcc caa    100
Ala Lys Arg Lys Gly Thr Arg Ser Val Ser Thr Leu Thr Pro Ser Gln
         15                  20                  25 ctg gct agg aag agg gca aac gac aga gaa gca cag agg gcc att cgt    148
Leu Ala Arg Lys Arg Ala Asn Asp Arg Glu Ala Gln Arg Ala Ile Arg
 30                  35                  40 gcg cgg aca aag gaa cac atc gaa cga ctc gaa agg gag gtc gaa gag    196
Ala Arg Thr Lys Glu His Ile Glu Arg Leu Glu Arg Glu Val Glu Glu
45                  50                  55                  60 ctc aag agc aag cag aac cgc gac gag acc ctc caa gaa ctc atc agg    244
Leu Lys Ser Lys Gln Asn Arg Asp Glu Thr Leu Gln Glu Leu Ile Arg
                 65                  70                  75 aag aac aag tac ctt gag aag gag att gcc agg ctg cgc gag act tat    292
Lys Asn Lys Tyr Leu Glu Lys Glu Ile Ala Arg Leu Arg Glu Thr Tyr
             80                  85                  90 ggc atc ccc acc ccg cca aca tct cac cca tat gcg ccg tcc atc tac    340
Gly Ile Pro Thr Pro Pro Thr Ser His Pro Tyr Ala Pro Ser Ile Tyr
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 95  |     |     |     |     | 100 |     |     |     |     | 105 |     |     |     |     |
| gac | gac | tct | gca | gtt | tcc | agc | cgg | aca | tca | tca | tct | ttt | ggg | caa | cat | 388 |
| Asp | Asp | Ser | Ala | Val | Ser | Ser | Arg | Thr | Ser | Ser | Ser | Phe | Gly | Gln | His |     |
|     |     | 110 |     |     |     |     | 115 |     |     |     |     | 120 |     |     |     |     |
| tcg | cca | gac | tac | cat | cag | gtc | gga | gag | tat | gga | gct | tcc | tac | atg | aca | 436 |
| Ser | Pro | Asp | Tyr | His | Gln | Val | Gly | Glu | Tyr | Gly | Ala | Ser | Tyr | Met | Thr |     |
| 125 |     |     |     |     | 130 |     |     |     |     | 135 |     |     |     |     | 140 |     |
| acc | ccc | gag | cct | tcc | gaa | ccg | tgg | aca | tca | gtc | tta | cct | tgc | tcc | aat | 484 |
| Thr | Pro | Glu | Pro | Ser | Glu | Pro | Trp | Thr | Ser | Val | Leu | Pro | Cys | Ser | Asn |     |
|     |     |     |     | 145 |     |     |     |     | 150 |     |     |     |     | 155 |     |     |
| gtt | tca | agc | cca | gca | tcg | tcc | gga | agt | gca | gaa | gaa | tac | gga | tac | atc | 532 |
| Val | Ser | Ser | Pro | Ala | Ser | Ser | Gly | Ser | Ala | Glu | Glu | Tyr | Gly | Tyr | Ile |     |
|     |     |     | 160 |     |     |     |     | 165 |     |     |     |     | 170 |     |     |     |
| ccg | acc | agt | gtt | ccc | gcc | gga | att | gaa | gga | ctc | cct | ccc | acg | tcg | cgt | 580 |
| Pro | Thr | Ser | Val | Pro | Ala | Gly | Ile | Glu | Gly | Leu | Pro | Pro | Thr | Ser | Arg |     |
|     |     | 175 |     |     |     |     | 180 |     |     |     |     | 185 |     |     |     |     |
| gtt | ggt | gcc | tgc | atg | aaa | tat | gag | gat | atg | gat | aac | gaa | aac | gga | tac | 628 |
| Val | Gly | Ala | Cys | Met | Lys | Tyr | Glu | Asp | Met | Asp | Asn | Glu | Asn | Gly | Tyr |     |
|     |     | 190 |     |     |     |     | 195 |     |     |     |     | 200 |     |     |     |     |
| ccc | cga | agc | aac | ggc | gtc | ccg | atg | ccc | cca | acc | tat | atg | cac | cag | cag | 676 |
| Pro | Arg | Ser | Asn | Gly | Val | Pro | Met | Pro | Pro | Thr | Tyr | Met | His | Gln | Gln |     |
| 205 |     |     |     |     | 210 |     |     |     |     | 215 |     |     |     |     | 220 |     |
| cag | tgg | ccc | gta | cca | tac | agt | gca | acc | gtt | tac | tac | ccc | caa | tcg | ccg | 724 |
| Gln | Trp | Pro | Val | Pro | Tyr | Ser | Ala | Thr | Val | Tyr | Tyr | Pro | Gln | Ser | Pro |     |
|     |     |     |     | 225 |     |     |     |     | 230 |     |     |     |     | 235 |     |     |
| gct | ctc | tgagcggcta | agggtcattt | ggctcccctc | cgtcgctggt | gaggagccaa |     |     |     |     |     |     |     |     |     | 780 |
| Ala | Leu |     |     |     |     |     |     |     |     |     |     |     |     |     |     |     |

```
gtcgggaccg  agatgttaa   atagtgttag  ccgccaccgt  gtcacgacaa  tggtctcaca     840
aaatcaatcc  ggcgacgccc  gaaatgggca  aaaacttgaa  ttcaaagaga  cgaaagcgaa     900
cgacgaattg  gacgacagag  aacatcgaac  ccgacctcct  tcgactcgac  ccagtcatca     960
tttcggttga  tcaagaaatt  attctagaaa  acccaaacgc  cggttttcga  dacagcatta    1020
gccaattttc  ttgctcatta  acccgagact  ttgaatgcat  tagcgtgagg  gagtgggcca    1080
gcggcggtaa  caaacaaacc  aggcataact  ccaacgggat  ttgtctgttc  ggatgttcca    1140
gcgcggggac  aacatcatca  aggccttgaa  cattcgaccg  atattcgatc  agatcagttc    1200
ctcaccgccg  aactcccgaa  gctcggcacg  ataaaccctg  aagccattgt  cacctgaaaa    1260
cattcgcctt  ttttttttgt  tattccgatg  ctcgttcgca  acactacgtt  ttagttcgac    1320
ctgtcacaca  ttgccgccgc  gcacgtgtgc  caccactagt  acagcttgtt  accggaccga    1380
acaacgtttt  tttcgccacc  gtgcgaccct  ggtcccaagt  ggcttggtgt  tgttgcttgc    1440
aaaaaaaacc  tccgacaaac  caagtccccc  gggctttatt  agtgtatgtc  atcacgcacc    1500
ccacaagagc  ctcccgtcac  tttgctgtca  gcatcttgat  ggcaggcggg  gtgaccggcg    1560
tgaacggcca  aaaggcgtag  gctttgcgca  gtctctccaa  caactttaaa  gggcaattgc    1620
gcttagcctt  ggccagaggt  gtcttagctg  gataaaaaa   aacacatatt  ctattcttat    1680
ttcgtttcct  tgcgctagcg  tactgcaaca  attttcatat  aattttttaca  ccacaattta    1740
gggaggttgg  ctgatttgga  cggcggcgtc  gtggaggtta  ctcatatatc  ggcgtatcaa    1800
gaaagctcat  taccaaagct  gtatttgctt  tttgtttctt  gtatatatag  actgcattgc    1860
tcttgtcttg  ttcatatgga  gtggacttgt  ctttgtgtgg  ttggagtctg  ggagcatatt    1920
attgggtgtg  aataacatag  gttgggaatc  aaaaaaaaa   aaaaaaaa                  1969
```

<210> SEQ ID NO 3

```
<211> LENGTH: 238
<212> TYPE: PRT
<213> ORGANISM: Magnaporthe grisea

<400> SEQUENCE: 3

Met Thr Arg Ser Pro Ser Ala Glu Pro Ser Lys Pro Ala Lys Arg Lys
1               5                   10                  15

Gly Thr Arg Ser Val Ser Thr Leu Thr Pro Ser Gln Leu Ala Arg Lys
            20                  25                  30

Arg Ala Asn Asp Arg Glu Ala Gln Arg Ala Ile Arg Ala Arg Thr Lys
        35                  40                  45

Glu His Ile Glu Arg Leu Glu Arg Val Glu Glu Leu Lys Ser Lys
    50                  55                  60

Gln Asn Arg Asp Glu Thr Leu Gln Glu Leu Ile Arg Lys Asn Lys Tyr
65                  70                  75                  80

Leu Glu Lys Glu Ile Ala Arg Leu Arg Glu Thr Tyr Gly Ile Pro Thr
                85                  90                  95

Pro Pro Thr Ser His Pro Tyr Ala Pro Ser Ile Tyr Asp Asp Ser Ala
            100                 105                 110

Val Ser Ser Arg Thr Ser Ser Ser Phe Gly Gln His Ser Pro Asp Tyr
        115                 120                 125

His Gln Val Gly Glu Tyr Gly Ala Ser Tyr Met Thr Thr Pro Glu Pro
    130                 135                 140

Ser Glu Pro Trp Thr Ser Val Leu Pro Cys Ser Asn Val Ser Ser Pro
145                 150                 155                 160

Ala Ser Ser Gly Ser Ala Glu Tyr Gly Tyr Ile Pro Thr Ser Val
                165                 170                 175

Pro Ala Gly Ile Glu Gly Leu Pro Pro Thr Ser Arg Val Gly Ala Cys
            180                 185                 190

Met Lys Tyr Glu Asp Met Asp Asn Glu Asn Gly Tyr Pro Arg Ser Asn
        195                 200                 205

Gly Val Pro Met Pro Pro Thr Tyr Met His Gln Gln Gln Trp Pro Val
    210                 215                 220

Pro Tyr Ser Ala Thr Val Tyr Tyr Pro Gln Ser Pro Ala Leu
225                 230                 235

<210> SEQ ID NO 4
<211> LENGTH: 783
<212> TYPE: DNA
<213> ORGANISM: Neurospora crassa
<220> FEATURE:
<221> NAME/KEY: CDS
<222> LOCATION: (1)..(783)

<400> SEQUENCE: 4 atg gct cgg tct cct cct gct ccc act acc ggg gac aat aag ccg ggt       48
Met Ala Arg Ser Pro Pro Ala Pro Thr Thr Gly Asp Asn Lys Pro Gly
1               5                   10                  15 acg gtg aag agg aaa ggc acg aga agc gtc tct acc ctc acg cct tca       96
Thr Val Lys Arg Lys Gly Thr Arg Ser Val Ser Thr Leu Thr Pro Ser
            20                  25                  30 cag cta gct agg aag cga gca aat gat cgg gaa gcg caa cgc gca ata      144
Gln Leu Ala Arg Lys Arg Ala Asn Asp Arg Glu Ala Gln Arg Ala Ile
        35                  40                  45 aga gct cgc act aag gag ctc att gaa agg tta caa cgc gaa tta gaa      192
Arg Ala Arg Thr Lys Glu Leu Ile Glu Arg Leu Gln Arg Glu Leu Glu
    50                  55                  60 gga tca agg gga agg gag aac cgc gat gga atg gtt cgt gaa ctg ctt      240
```

```
                                              -continued

Gly Ser Arg Gly Arg Glu Asn Arg Asp Gly Met Val Arg Glu Leu Leu
 65                  70                  75                  80 cag aag aac aag gca ttg gaa cac gaa gta cga gca ttg agg gaa gcc       288
Gln Lys Asn Lys Ala Leu Glu His Glu Val Arg Ala Leu Arg Glu Ala
                 85                  90                  95 ctt ggc atc ggg aac cga ccg ttt cct caa tct ggc tac gag gtg gat       336
Leu Gly Ile Gly Asn Arg Pro Phe Pro Gln Ser Gly Tyr Glu Val Asp
            100                 105                 110 gga ctg cca act tcg cca tca gca gtt cca ggt cgc ggg gca tct atc       384
Gly Leu Pro Thr Ser Pro Ser Ala Val Pro Gly Arg Gly Ala Ser Ile
        115                 120                 125 ccc caa ggc tcc acg gac tat ggt gca ccg aca agc ttt ggg tca tct       432
Pro Gln Gly Ser Thr Asp Tyr Gly Ala Pro Thr Ser Phe Gly Ser Ser
    130                 135                 140 tac ctc cct act cct gaa cct tgt gag gca tgg cct ccg gtc gtc cct       480
Tyr Leu Pro Thr Pro Glu Pro Cys Glu Ala Trp Pro Pro Val Val Pro
145                 150                 155                 160 gtc tct tca gtc act gtt tct tca gtg gtt tca agt ccg tcg tca tcc       528
Val Ser Ser Val Thr Val Ser Ser Val Val Ser Ser Pro Ser Ser Ser
                165                 170                 175 acg ggg cat cct gat gag tac gcg gct agc cac gtc ccc aca agc gtc       576
Thr Gly His Pro Asp Glu Tyr Ala Ala Ser His Val Pro Thr Ser Val
            180                 185                 190 cct tct tcc ttg atg gac tca tct gta atg ggt caa gct acg gga atc       624
Pro Ser Ser Leu Met Asp Ser Ser Val Met Gly Gln Ala Thr Gly Ile
        195                 200                 205 tct tgc ctg gac ggt atg aag gtc aac tac gac gag att gaa gct gac       672
Ser Cys Leu Asp Gly Met Lys Val Asn Tyr Asp Glu Ile Glu Ala Asp
    210                 215                 220 cgc gga tac tgt ccg acc agc gtt cca cag ccg caa tcc tct tat ctc       720
Arg Gly Tyr Cys Pro Thr Ser Val Pro Gln Pro Gln Ser Ser Tyr Leu
225                 230                 235                 240 ccc cag cag tcc tgg tcc atg tac ccc aca tca act tac tat cca caa       768
Pro Gln Gln Ser Trp Ser Met Tyr Pro Thr Ser Thr Tyr Tyr Pro Gln
                245                 250                 255 tcg cct acg gtt tga                                                   783
Ser Pro Thr Val
            260

<210> SEQ ID NO 5
<211> LENGTH: 260
<212> TYPE: PRT
<213> ORGANISM: Neurospora crassa

<400> SEQUENCE: 5

Met Ala Arg Ser Pro Pro Ala Pro Thr Thr Gly Asp Asn Lys Pro Gly
  1               5                  10                  15

Thr Val Lys Arg Lys Gly Thr Arg Ser Val Ser Thr Leu Thr Pro Ser
                 20                  25                  30

Gln Leu Ala Arg Lys Arg Ala Asn Asp Arg Glu Ala Gln Arg Ala Ile
            35                  40                  45

Arg Ala Arg Thr Lys Glu Leu Ile Glu Arg Leu Gln Arg Glu Leu Glu
        50                  55                  60

Gly Ser Arg Gly Arg Glu Asn Arg Asp Gly Met Val Arg Glu Leu Leu
 65                  70                  75                  80

Gln Lys Asn Lys Ala Leu Glu His Glu Val Arg Ala Leu Arg Glu Ala
                 85                  90                  95

Leu Gly Ile Gly Asn Arg Pro Phe Pro Gln Ser Gly Tyr Glu Val Asp
            100                 105                 110
```

-continued

```
Gly Leu Pro Thr Ser Pro Ser Ala Val Pro Gly Arg Gly Ala Ser Ile
        115                 120                 125

Pro Gln Gly Ser Thr Asp Tyr Gly Ala Pro Thr Ser Phe Gly Ser Ser
    130                 135                 140

Tyr Leu Pro Thr Pro Glu Pro Cys Glu Ala Trp Pro Pro Val Val Pro
145                 150                 155                 160

Val Ser Ser Val Thr Val Ser Ser Val Val Ser Ser Pro Ser Ser Ser
                165                 170                 175

Thr Gly His Pro Asp Glu Tyr Ala Ala Ser His Val Pro Thr Ser Val
            180                 185                 190

Pro Ser Ser Leu Met Asp Ser Ser Val Met Gly Gln Ala Thr Gly Ile
        195                 200                 205

Ser Cys Leu Asp Gly Met Lys Val Asn Tyr Asp Glu Ile Glu Ala Asp
    210                 215                 220

Arg Gly Tyr Cys Pro Thr Ser Val Pro Gln Pro Gln Ser Ser Tyr Leu
225                 230                 235                 240

Pro Gln Gln Ser Trp Ser Met Tyr Pro Thr Ser Thr Tyr Tyr Pro Gln
                245                 250                 255

Ser Pro Thr Val
            260
```